(12) United States Patent
Achilias et al.

(10) Patent No.: US 10,076,118 B2
(45) Date of Patent: Sep. 18, 2018

(54) METHODS OF MAKING ANTIMICROBIAL POLY(METHYL METHACRYLATE) /SILVER NANOCOMPOSITES AND INHIBITING BACTERIAL GROWTH WITH POLY(METHYL METHACRYLATE) /SILVER NANOCOMPOSITES

(71) Applicant: KING FAHD UNIVERSITY OF PETROLEUM AND MINERALS, Dhahran (SA)

(72) Inventors: Dimitris S. Achilias, Thessaloniki (GR); Mohammad Nahid Siddiqui, Dhahran (SA); Halim Hamid Redhwi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/391,509

(22) Filed: Dec. 27, 2016

(65) Prior Publication Data

US 2017/0181439 A1 Jun. 29, 2017

Related U.S. Application Data

(60) Provisional application No. 62/271,865, filed on Dec. 28, 2015.

(51) Int. Cl.
*A01N 59/16* (2006.01)
*A01N 25/10* (2006.01)
*A01N 25/28* (2006.01)

(52) U.S. Cl.
CPC ............ *A01N 59/16* (2013.01); *A01N 25/28* (2013.01)

(58) Field of Classification Search
CPC ................................ A01N 59/16; A01N 25/10
See application file for complete search history.

(56) References Cited

U.S. PATENT DOCUMENTS 8,779,023 B2 7/2014 Whang et al.
9,334,386 B2 5/2016 Alsharaeh et al.

FOREIGN PATENT DOCUMENTS

CN 102850477 A 1/2013

OTHER PUBLICATIONS

S. Borse, et al. "Photochemically assisted one-pot synthesis of PMMA embedded silver nanoparticles: antibacterial efficacy and water treatment" http://pubs.rsc.org/en/Content/ArticleLanding/2016/RA/C6RA08397H#!divAbstract, Jun. 1, 2016, vol. 6, Issue. 61, pp. 56674-56683.

(Continued)

*Primary Examiner* — Jianfeng Song
(74) *Attorney, Agent, or Firm* — Oblon, McClelland, Maier & Neustadt, L.L.P.

(57) ABSTRACT

A method of making an antimicrobial poly(methyl methacrylate) (PMMA)/silver nanocomposite comprising PMMA and silver nanoparticles. The method includes reacting at least one silver salt with a methyl methacrylate (MMA) monomer in at least one organic solvent free of water and in the presence of at least one organic free radical initiator to polymerize the MMA monomer to form the PMMA by free radical polymerization while reducing in-situ the silver salt to form the silver nanoparticles, wherein the silver nanoparticles have an average particle size of 35-60 nm, and wherein the PMMA forms a matrix that encloses the silver nanoparticles.

16 Claims, 16 Drawing Sheets

(56) References Cited

OTHER PUBLICATIONS

A. Akhavan, et al., "Polymethylmethacrylate/Silver Nanocomposite Prepared by γ-Ray" http://en.journals.sid.ir/ViewPaper.aspx?ID=177833, 2010, vol. 4, Issue. 50, pp. 80-84.
L. Wang, et al., "A one-pot approach to the preparation of silver-PMMA "shell-core" nanocomposite" http://link.springer.com/article/10.1007/s00396-005-1401-7, Jan. 2006, vol. 284, Issue.4, pp. 449-454.
A. M. Youssef et al., "A novel approach to prepare poly (methyl methacrylate)/Ag nanocomposites" http://www.tsijournals.com/abstract/a-novel-approach-to-prepare-poly-methyl-methacrylateag-nanocomposites-4366.html, 2013, vol. 7, Issue. 6, pp. 217-223.

METHODS OF MAKING ANTIMICROBIAL POLY(METHYL METHACRYLATE) /SILVER NANOCOMPOSITES AND INHIBITING BACTERIAL GROWTH WITH POLY(METHYL METHACRYLATE) /SILVER NANOCOMPOSITES

CROSS-REFERENCE TO RELATED APPLICATIONS

This application claims the benefit of U.S. Provisional Application No. 62/271,865, filed Dec. 28, 2015. The provisional application identified above is incorporated here by reference in its entirety.

BACKGROUND OF THE INVENTION

Technical Field

The present disclosure relates to methods of making an antimicrobial poly(methyl methacrylate) (PMMA)/silver nanocomposite comprising PMMA and silver nanoparticles and methods of inhibiting bacterial growth using the antimicrobial PMMA/silver nanocomposite.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Polymeric materials with antimicrobial characteristics are needed in many applications, such as water treatment agents and equipment, household goods, textiles, products that prevent food spoilage, and medical devices including catheters, prosthetics, implants, and ophthalmic devices.

It is an object of this disclosure to provide a method of making an antimicrobial poly(methyl methacrylate) (PMMA)/silver nanocomposite comprising PMMA and silver nanoparticles and a method of inhibiting bacterial growth using the antimicrobial PMMA/silver nanocomposite. The disclosed PMMA/silver nanocomposite is an effective antimicrobial material, has a low silver content, and is inexpensive to make.

BRIEF SUMMARY OF THE INVENTION

According to a first aspect, the present disclosure relates to a method of making an antimicrobial poly(methyl methacrylate) (PMMA)/silver nanocomposite comprising PMMA and silver nanoparticles. The method includes polymerizing and/or reacting methyl methacrylate (MMA) monomer in at least one organic solvent, preferably free of water, and in the presence of at least one organic free radical initiator and at least one silver salt to form the PMMA by free radical polymerization while reducing in-situ the silver salt to form the silver nanoparticles, wherein the silver nanoparticles have an average particle size of 35-60 nm, and wherein the PMMA forms a matrix that encloses the silver nanoparticles.

In one or more embodiments, the at least one silver salt is at least one selected from the group consisting of a silver oxide, a silver carbide, a silver nitride, a silver boride, a silver borate, a silver benzoate, a silver sulfide, a silver myristate, a silver stearate, a silver oleate, a silver gluconate, a silver adipate, a silver silicate, a silver sulfate, a silver phosphide, a silver halide, a silver hydride, a silver nitrate, a silver carbonate, a silver sulfadiazine, a silver acetate, a silver lactate, a silver citrate, and an alkali silver thiosulphate.

In one or more embodiments, the at least one organic free radical initiator is at least one selected from the group consisting of an organic peroxide, a perester, a peroxydicarbonate, and an azo initiator.

In one or more embodiments, the at least one organic free radical initiator is at least one selected from the group consisting of benzoyl peroxide, dilauroyl peroxide, didecanoyl peroxide, diacetyl peroxide, di(3,5,5-trimethylhexanoyl) peroxide, cumene hydroperoxide, dimethylparatoluidine (DMPT), and allyl thiourea (T).

In one or more embodiments, the at least one organic free radical initiator is at least one diacyl peroxide at an initial concentration of 0.02-0.04 M.

In one or more embodiments, the silver salt is solely reduced by at least one free radical formed during the free radical polymerization of the MMA monomer.

In one or more embodiments, the at least one free radical comprises a hydrogen radical.

In one or more embodiments, the PMMA/silver nanocomposite comprises the silver nanoparticles in an amount of 0.03-0.18% of the total weight of the PMMA/silver nanocomposite.

In one or more embodiments, the PMMA/silver nanocomposite has a number average molecular weight of 120,000-165,000.

In one or more embodiments, the PMMA/silver nanocomposite has a weight average molecular weight of 280,000-370,000.

In one or more embodiments, the PMMA/silver nanocomposite has a glass transition temperature of 80-95° C.

In one or more embodiments, the reacting is performed at a temperature of 70-90° C.

According to a second aspect, the present disclosure relates to a method of inhibiting a growth of bacteria. The method includes contacting the bacteria or a medium comprising the bacteria with an effective amount of an antimicrobial poly(methyl methacrylate) (PMMA)/silver nanocomposite comprising PMMA and silver nanoparticles, wherein the silver nanoparticles have an average particle size of 35-60 nm, and wherein the poly(methyl methacrylate) forms a matrix that encloses the silver nanoparticles.

In one or more embodiments, the medium comprising the bacteria is a fluid, a semi-solid, or a solid.

In one or more embodiments, the antimicrobial PMMA/silver nanocomposite is disposed on a surface of a substrate to form a substrate coated with a membrane of the PMMA/silver nanocomposite.

In one or more embodiments, the substrate comprises at least one selected from the group consisting of glass, stone, masonry, a metal, wood, a plastic, concrete, a fiber, a textile, a yarn, a ceramic, paper, and paint.

In one or more embodiments, the medium comprising the bacteria is a fluid, and wherein the PMMA/silver nanocomposite is disposed in a fixed bed reactor or fluidized bed reactor and the contacting involves passing the fluid through the fixed bed reactor or fluidized bed reactor.

In one or more embodiments, the effective amount of the antimicrobial PMMA/silver nanocomposite lies in the range of 50-200 µg/ml medium comprising the bacteria.

In one or more embodiments, the PMMA/silver nanocomposite comprises the silver nanoparticles in an amount of 0.07-0.11% of the total weight of the PMMA/silver nanocomposite, and 70-95% of the growth of bacteria is inhibited as compared to a growth of the bacteria which do not, or the medium of which does not, contact the PMMA/silver nanocomposite but which are otherwise grown under the same conditions.

In one or more embodiments, the bacteria are at least one selected from the group consisting of bacteria of the genus *Bacillus*, bacteria of the genus *Escherichia*, and bacteria of the genus *Staphylococcus*.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
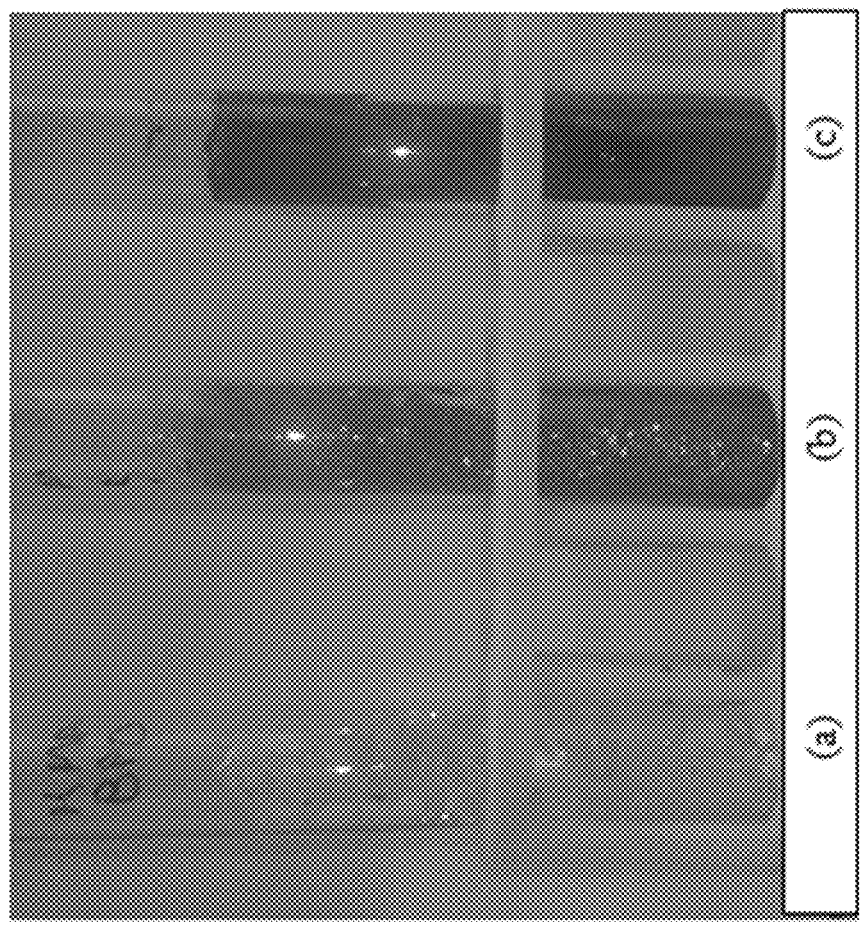
FIG. 1 shows in test tube (a) a polymer obtained after polymerization of MMA by BPO at 80° C. in the absence of $AgNO_3$, in test tube (b) a polymer obtained after polymerization of MMA by BPO at 80° C. in the presence of 2% by volume relative to the volume of the MMA monomers of 0.1 M $AgNO_3$ dissolved in DMF, and in test tube (c) a polymer obtained after polymerization of MMA by BPO at 80° C. in the presence of 6% by volume relative to the volume of the MMA monomers of 0.1 M $AgNO_3$ dissolved in DMF.

The present disclosure incorporates by reference in its entirety the following publication: Synthesis, characterization and reaction kinetics of PMMA/silver nanocomposites prepared via in situ radical polymerization, Mohammad Nahid Siddiqui, Halim Hamid Redhwi, Efthymia Vakalopoulou, Ioannis Tsagkalias, Maria D. Ioannidou, and Dimitris S. Achilias, European Polymer Journal, Volume 72, November 2015, Pages 256-269.

According to a first aspect, the present disclosure relates to a method of making an antimicrobial poly(methyl methacrylate) (PMMA)/silver nanocomposite comprising PMMA and silver nanoparticles. The method includes polymerizing and/or reacting methyl methacrylate (MMA) monomer in at least one organic solvent, preferably free of water, and in the presence of at least one silver salt and at least one organic free radical initiator to polymerize the MMA monomer to form the PMMA by free radical polymerization while reducing in-situ the silver salt to form the silver nanoparticles, wherein the silver nanoparticles have an average particle size of 35-60 nm, and wherein the PMMA forms a matrix that encloses the silver nanoparticles.

In one embodiment, the reaction mixture of the disclosed method includes only one type of monomer, i.e. the monomers of MMA, to form the PMMA/silver nanocomposite in which PMMA is the only polymer present.

In another embodiment, the reaction mixture of the disclosed method includes one or more other types of monomers besides the monomers of MMA, such that the resulting PMMA/silver nanocomposite comprises PMMA and one or more other types of polymers formed from the corresponding one or more types of monomers by free radical polymerization. Non-limiting examples of the other types of polymers include polyvinyl alcohol, poly ethylene glycol, ethyl cellulose, polyolefins, polyesters, nonpeptide polyamines, polyamides, polycarbonates, polyalkenes, polyvinyl ethers, polyglycolides, cellulose ethers, polyvinyl halides, polyhydroxyalkanoates, polyanhydrides, polystyrenes, polyacrylates, polymethacrylates other than PMMA, polyurethanes, polypropylene, polybutylene terephthalate, polyethylene terephthalate, nylon 6, nylon 6,6, nylon 4,6, nylon 12, phenolic resins, urea resins, epoxy resins, silicone polymers, polycarbonates, polyethylene vinylacetate, polyethylene ethyl acrylate, polylactic acid, polysaccharides, polytetrafluoroethylene, polyvinylidenes, polyphosphazines, chlorinated polyethylenes, polysulfones and copolymers and blends thereof. More specific examples of polymethacrylates other than PMMA include poly(bisphenol glycidyl methacrylate (Bis-GMA)), poly(triethylene glycol dimethacrylate (TEGDMA)), poly(2-hydroxyethyl methacrylate (HEMA)), poly(pryomellitic acid diethylmethacrylate (PMDM)), poly(pyromellitic acid glycerol dimethacrylate (PMGDM)), and polyurethane dimethacrylate (UDMA)).

The mass ratio of the MMA monomers to the other types of monomers may vary without limitation, depending on, for example, the desired mechanical and antimicrobial property and thermal stability of the PMMA/silver nanocomposite formed. Exemplary mass ratios include 10:1-1:10, 5:1-1:5, 2:1-1:2, or 1:1.

"Antimicrobial" means that the PMMA/silver nanocomposite exhibits one or more of the following properties: inhibition of the adhesion of bacteria or other microbes to the PMMA/silver nanocomposite; inhibition of the growth of bacteria or other microbes on the PMMA/silver nanocomposite or in a medium containing both the bacteria or other microbes and the PMMA/silver nanocomposite; and/or killing of bacteria or other microbes on the surface of the PMMA/silver nanocomposite or in an area or medium surrounding or containing the PMMA/silver nanocomposite in comparison to an acrylate surface that does not contain Ag nanoparticles. Non-limiting examples of silver salts suitable for the method include a silver oxide, a silver carbide, a silver nitride, a silver boride, a silver borate, a silver benzoate, a silver sulfide, a silver myristate, a silver stearate, a silver oleate, a silver gluconate, a silver adipate, a silver silicate, a silver sulfate, a silver phosphide, a silver halide, a silver hydride, a silver nitrate, a silver carbonate, a silver sulfadiazine, a silver acetate, a silver lactate, a silver citrate, an alkali silver thiosulphate (e.g., sodium silver thiosulphate, potassium silver thiosulphate).

Silver is a precious metal. The disclosed method may be advantageously used to produce the PMMA/silver nanocomposite exhibiting an excellent antimicrobial activity with a very low amount of the silver salt in the reaction mixture. In some embodiments, the silver salt is present in an amount of 0.05-0.3%, or 0.1-0.2% of the weight of the MMA monomer in the reaction mixture, with the resulting PMMA/silver nanocomposite having a silver nanoparticle content of 0.03-0.18%, 0.05-0.15%, or 0.07-0.11% of the total weight of the PMMA/silver nanocomposite and a bacterial growth inhibition efficiency of 40-99%, 60-95%, 70-95%, or 90-95%.

In a preferred embodiment, the reaction mixture does not comprise water. The suitable organic solvent of the reaction mixture may be any liquid organic compound in which the silver salt and the monomer of MMA are soluble and which is substantially chemically unreactive with the silver salt and the monomer of MMA. Non-limiting examples of suitable organic solvents include dimethylformamide (DMF), dimethylaminoethyl methacrylate (DMAEMA), benzene, naphthalene, a lower alkyl (up to 11 carbon atoms) substituted benzenes (e.g. toluene), lower alkyl (up to 11 carbon atoms) substituted naphthalenes, and lower alkoxy (up to 11 carbon atoms) lower alkanes (up to 11 carbon atoms). More specific examples include, without limitation, benzene, toluene, xylene, ethylbenzene, trimethylbenzenes and their aromatic isomers, such as methylethylbenzene or cumenes, cymenes, naphthalene, methylnaphthalene; diethylether, dimethylether, amylether, methylethylether, anisole, phenetol, dioxane, tetrahydrofurane; acetone, methylethylketone, acetonylacetone, acetophenone, benzophenone; methanol, ethanol, propanol, butanols, amyl alcohols, glycol, butane diols; phenols, e.g. phenol, cresols, xylenols; chlorobenzene, bromobenzene, dichlorobenzene, chlorotoluene, chloroform, ethyl chloride, trichloroethylene; nitroethane, nitrobenzene, nitrotoluene; octene, decene, 1,5-octadiene, heptene, and hexene. The particular selection of the organic solvent in the reaction mixture depends on the chosen type of the free radical polymerization of MMA to form the PMMA according to the disclosed method. For example, if the free radical polymerization of MMA is chosen to be bulk polymerization to produce dry polymers, the PMMA or the PMMA/silver nanocomposite produced should not be soluble in the organic solvent selected. On the other hand, if the free radical polymerization of MMA is chosen to be solution polymerization, the organic solvent selected should be one where the PMMA or the PMMA/silver nanocomposite produced is soluble.

In some embodiments, the at least one organic free radical initiator is at least one selected from the group consisting of an organic peroxide (e.g. cumene hydroperoxide and diacyl peroxides, such as benzoyl peroxide, dilauroyl peroxide, didecanoyl peroxide, diacetyl peroxide, di(3,5,5-trimethylhexanoyl) peroxide), a perester (e.g. tert-butyl monoperoxymaleate, 2,5-dimethyl-2,5-di(2-ethylhexanoylperoxy) hexane, and tert-butyl peroxy-2-ethylhexanoate), a peroxydicarbonate (e.g. diisopropyl peroxydicarbonate, di(2-ethylhexyl) peroxydicarbonate, and dimyristyl peroxydicarbonate), an azo initiator and, more specifically, dimethylparatoluidine (DMPT) and allyl thiourea (T). Exemplary azo initiators include, without limitation, 2,2'-azobis(2-methylpropanenitrile), 1,1'-azobis(1-cyclohexanenitrile), 2,2'-azobis(2-methylbutanenitrile), 4,4'-azobis(4-cyanovaleric acid), 2,2'-azobis(methyl 2-methylpropanate), and 2,2'-azobis(2-phenylpropane).

Use of different individual organic free radical initiators or different combinations of organic free radical initiators at different concentrations or ratios affects the degree of chemical curing of the MMA monomer, which may unpredictably affect the silver release rate and thus the antimicrobial activity of the resulting PMMA/silver nanocomposite. In a preferred embodiment, a single diacyl peroxide, e.g. benzoyl peroxide (BPO), or a combination of diacyl peroxides, is used with the initial concentration of the diacyl peroxide(s) at 0.01-0.05M, more preferably 0.02-0.04 M in the reaction mixture.

Free radical polymerization is a method of polymerization by which a polymer forms by the successive addition of free radical building blocks. Free radical polymerization includes initiation, propagation, and termination.

Initiation is the first step of the polymerization process. During initiation, an active center is created from which a polymer chain is generated. Initiation has two steps. In the first step, one or two free radicals are created from the initiator molecules. In the second step, free radicals are transferred from the initiator molecules to the monomer units present to form a bigger free radical lengthened by the monomer units.

In a preferred embodiment, the initiator is an organic peroxide, more preferably a diacyl peroxide, or more preferably BPO, and the polymerizing and/or reacting is performed at a temperature of 60-100° C., more preferably 70-90° C., more preferably 75-85° C. to thermally decompose the initiator to produce the radicals for the initiation of the free radical polymerization of the MMA monomers.

During propagation, the bigger free radical reacts with another monomer and so on to form a longer and longer polymer chain.

However, the polymer chain does not grow indefinitely. During termination which is a random process, two free radicals each containing a polymer chain collide, and the growth of the two chains stops immediately because no new free radicals are formed, producing one of the final polymer molecules of different sizes.

In embodiments where the organic free radical initiator is benzoyl peroxide, the PMMA/silver nanocomposite is substantially free of transition metal catalysts that may be present in polymerization reactions requiring their use, such as metallocene catalysts used in Zeigler-Natta polymerization reactions.

In some embodiments, the polymerizing and/or reacting lasts 40-80 minutes, more preferably 50-70, more preferably 55-65 minutes.

Figure 2:
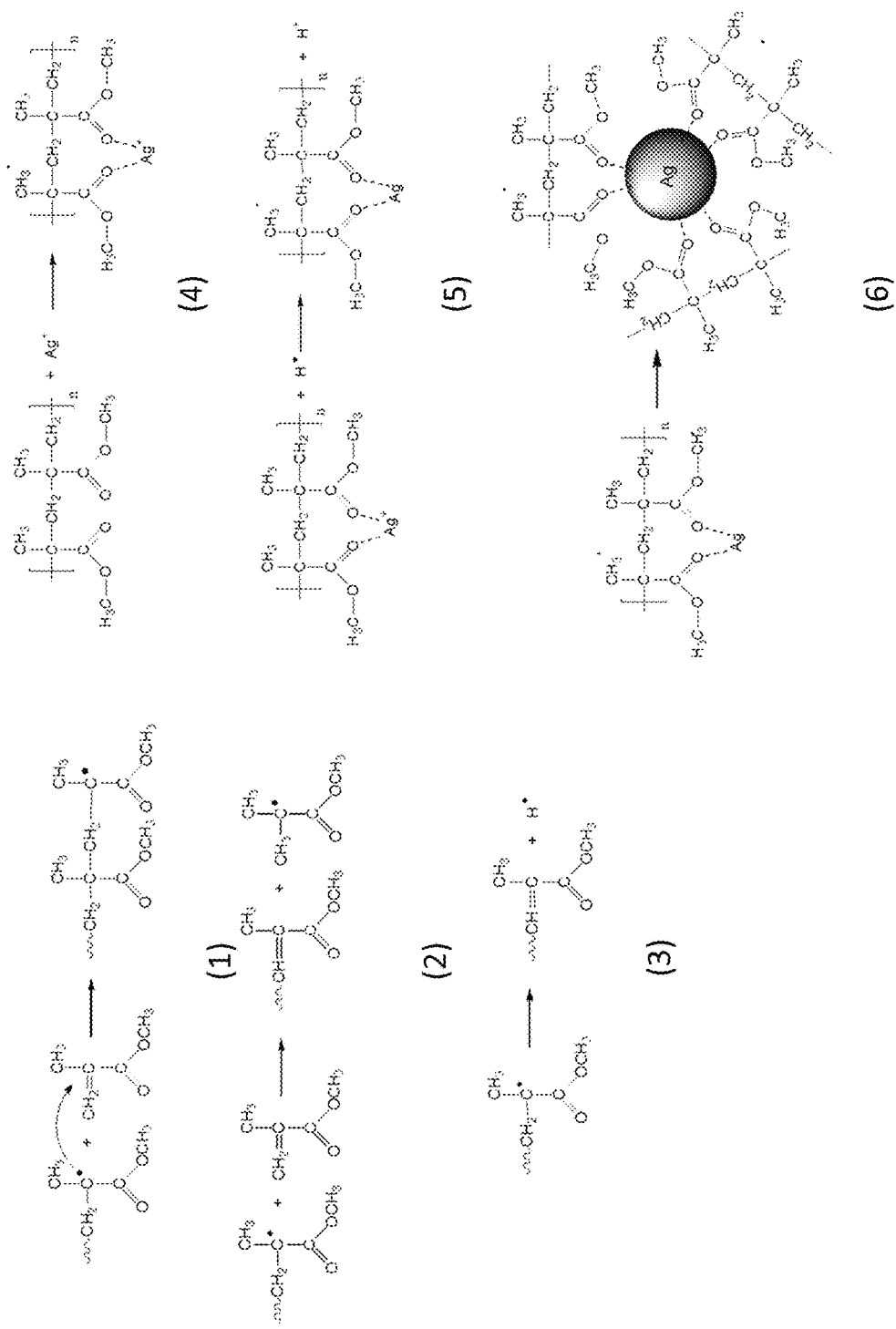
FIG. 2 is a schematic showing a possible mechanism for the in situ formation of Ag nanoparticles during the free radical polymerization of MMA to synthesize the PMMA/Ag nanocomposite.

In the disclosed method, silver ions from the silver salt are reduced to metallic silver in the form of silver nanoparticles in situ while the MMA monomers are polymerized to form the PMMA via free radical polymerization. In the resulting PMMA/silver nanocomposite, the silver nanoparticles are embedded in, or enclosed by in a matrix of the PMMA. Also in the disclosed method, the silver ions are reduced to the silver nanoparticles not directly by any of the chemicals supplied at the start of the reaction, i.e. the MMA monomer, the organic solvent, or the organic radical initiator, but by a free radical, for example, a hydrogen radical, that is formed during the free radical polymerization of the MMA monomers. The silver nanoparticles may be datively bound to the ester oxygens of methacrylate in the PMMA polymer matrix, such as is shown in FIG. 2.

In some embodiments, the silver nanoparticles in the PMMA/silver nanocomposite produced by the disclosed method have an average particle size of 35-60 nm, 40-50 nm, or 40-45 nm.

In some embodiments, the PMMA/silver nanocomposite produced by the disclosed method has a number average molecular weight (Mn) of 120,000-170,000, 130,000-165,000, 135,000-160,000, or 140,000-155,000.

In some embodiments, the PMMA/silver nanocomposite produced by the disclosed method has a weight average molecular weight (Mw) of 250,000-400,000, 280,000-380,000, or 300,000-350,000.

In some embodiments, the PMMA/silver nanocomposite produced by the disclosed method has a higher average molecular weight (Mz) of 500,000-800,000, 530,000-750,000, 560,000-730,000, or 600,000-700,000.

In some embodiments, the PMMA/silver nanocomposite produced by the disclosed method has a polydispersity index (Mw/Mn) of 2.0-2.5, or 2.2-2.4.

In some embodiments, the PMMA/silver nanocomposite produced by the disclosed method has a glass transition temperature of 70-98° C., 80-95° C., or 85-90° C.

According to a second aspect, the present disclosure relates to a method of inhibiting a growth of bacteria. The method includes contacting the bacteria or a medium comprising the bacteria with an effective amount of an antimicrobial poly(methyl methacrylate) (PMMA)/silver nanocomposite comprising PMMA and silver nanoparticles, wherein the silver nanoparticles have an average particle size of 35-60, 40-50, or 40-45 nm, and wherein the poly (methyl methacrylate) forms a matrix that encloses the silver nanoparticles. The antimicrobial poly(methyl methacrylate) (PMMA)/silver nanocomposite is preferably synthesized by the method described in the first aspect of the present disclosure, and has the same characteristics as those described in the first aspect.

The bacteria may be any individual type or strain of bacteria or their combinations. For example, the bacteria may be of Gram positive bacteria, Gram negative bacteria, antibiotic sensitive bacteria, or antibiotic resistant bacteria. In a preferred embodiment, the bacteria are at least one selected from the group consisting of bacteria of the genus *Bacillus* (e.g. *Bacillus cereus* and *Bacillus subtilis*), bacteria of the genus *Escherichia* (e.g. *Escherichia coli*), and bacteria of the genus *Staphylococcus* (e.g. *Staphylococcus aureus*).

The medium comprising the bacteria may be a fluid medium, which includes a liquid medium, such as water, an aqueous solution, an oil, or a mixture of oil and water, and a gas medium, such as air. The medium may also be a semi-solid medium, such as a gel, a paste, a cream, or an agar. The medium may also be a solid medium, such as a particulate solid medium, e.g. sand and soil, or a surface of a solid object, e.g. a surface of a table or a medical device or instrument.

The extent of growth inhibition of the bacteria may be quantified in various ways. For example, it may be quantified by determining the ratio of the number of the bacteria grown while the bacteria or the medium comprising the bacteria contacts the antimicrobial PMMA/silver nanocomposite to the number of the bacteria grown without the bacteria or the medium comprising the bacteria contacting the antimicrobial PMMA/silver nanocomposite but otherwise under the same conditions. The number of the bacteria can be determined and reported as CFU, or colony forming units. One colony is formed by a single bacterium when the bacteria are plated at a suitable dilution for single colony formation. This is a standard technique known to microbiologists.

Alternatively, when the bacteria are present in a liquid medium contacting or not the antimicrobial PMMA/silver nanocomposite, the number of the bacteria is proportional to and thus may be quantified by optical density (OD) of the liquid bacterial culture at a wavelength of 590-610 nm, or 600 nm. The lower is the ratio of the OD of the liquid bacterial culture contacting the antimicrobial PMMA/silver nanocomposite to the OD of the liquid bacterial culture not contacting the antimicrobial PMMA/silver nanocomposite, the higher is the efficiency of growth inhibition of the bacteria.

Still alternatively, growth inhibition of the bacteria may be quantified by comparing the metabolic activity of the bacteria which contact, or the medium of which contacts, the antimicrobial PMMA/silver nanocomposite with the metabolic activity of the bacteria which do not, or the medium of which does not, contact the antimicrobial PMMA/silver nanocomposite but which are otherwise grown under the same conditions. Any suitable assay for bacterial metabolic activity and/or any suitable biomarker for bacterial metabolic activity may be used or examined. For example, the metabolic activity of the bacteria can be measured by the AlamarBlue® assay. "AlamarBlue" is a registered trademark name by TREK Diagnostic Systems for an assay that is provided, e.g. by Invitrogen or Promega. The AlamarBlue assay uses the natural reducing power of living bacteria to convert resazurin, a cell permeable compound that is blue in color and virtually non-fluorescent. Upon entering metabolically active bacteria, resazurin, the non-fluorescent indicator dye, is reduced to bright red-fluorescent resorufin. The amount of fluorescence produced is proportional to the number of living bacteria. The fluorescence may be detected with any plate reader or fluorescence spectrophotometer using 560 nm (for excitation)/590 nm (for emission) filter settings. Alternatively, the absorbance of AlamarBlue® can be read on a UV-Vis spectrophotometer at 570 nm.

Still alternatively, growth inhibition of the bacteria may be determined by an agar diffusion test (Kirby-Bauer testing), in which a wafer (e.g. a filter paper disk) impregnated or not with the antimicrobial PMMA/silver nanocomposite, or impregnated with a known reference antimicrobial agent is placed on an agar plate where the bacteria have been plated. After incubation of the plate, the diameter of the zone of inhibition on the plate tested with the antimicrobial PMMA/silver nanocomposite may be compared with the diameter of the zone of inhibition on the control plate (without any antimicrobial agent) and on the plate tested with the known reference antimicrobial agent.

In a preferred embodiment, the PMMA/silver nanocomposite comprises the silver nanoparticles in an amount of 0.03-0.18%, 0.05-0.15%, or 0.07-0.11% of the total weight of the PMMA/silver nanocomposite, and 40-99%, 60-95%, 70-95%, or 90-95% of the growth of the bacteria is inhibited as compared to a growth of the bacteria which do not, or the medium of which does not, contact the PMMA/silver nanocomposite but which are otherwise grown under the same conditions.

In one embodiment, the bacteria are present in a fluid medium, which may be a liquid, e.g. water, an aqueous solution, and oil, or a gas, e.g. air, or a particulate solid medium, such as soil and sand. The contacting of the fluid or the particulate solid medium comprising the bacteria with the PMMA/silver nanocomposite may be performed by mixing an effective amount of the PMMA/silver nanocomposite with a certain volume of the fluid or the particulate solid medium, preferably with the mixture under constant agitation (e.g. stirring, shaking, or vortexing). The PMMA/silver nanocomposite is preferably in the form of powder, particles, or small pellets to increase the surface area of the PMMA/silver nanocomposite contacting the fluid or the particulate solid medium or the bacteria. The effective amount of the PMMA/silver nanocomposite per unit volume of the fluid or the particulate solid medium may vary depending on the composition, particularly the silver nanoparticle size and content of the PMMA/silver nanocomposite, the initial number and the type of the bacteria in the fluid or the particulate solid medium, the efficiency of the contacting determined by, for example, the intensity of agitation of the mixture, the efficiency of growth inhibition of the bacteria desired, etc., and may typically range from about 20-400 µg/ml, 30-300 µg/ml, 50-200 µg/ml, 80-150 µg/ml, 100-120 µg/ml of the fluid or the particulate solid medium.

To expand the applications of the antimicrobial PMMA/silver nanocomposite and/or increase the efficiency of the contacting of the bacteria or the medium comprising the bacteria with the PMMA/silver nanocomposite, the PMMA/silver nanocomposite may be disposed on a surface of a substrate to form a substrate coated with a membrane of the PMMA/silver nanocomposite that can come into contact with the bacteria or the medium comprising the bacteria. In some embodiments, the thickness of the membrane of the PMMA/silver nanocomposite is 1-5000 µm, 10-3000 µm, 50-2000 µm, 100-1000 µm, 200-800 µm, or 400-600 µm. The substrate may comprise any suitable material which is inert or stable in the medium containing the bacteria and which provides a surface for the deposition of the PMMA/silver nanocomposite. Non-limiting examples of the suitable substrate material include glass (e.g. borosilicate glass, soda glass, or quartz), stone, masonry, metals (e.g. stainless steel, gold, aluminum, titanium, copper, and various metal alloys), wood, plastics (e.g. polycarbonate, polystyrene, nylon, and polyethylene), concrete, rubber, fibers, textiles, yarns, ceramics, paper, and paint. The substrate may be a piece of (medical) equipment, a building interior or exterior, a medical device, a tube, or an article or a part thereof which is exposed to bacteria or prone to contamination with bacteria. In some embodiments, the PMMA/silver nanocomposite membrane covers at least about 30%, at least about 50%, at least about 70%, at least about 90%, or at least about 95% of the substrate surface. Since the PMMA/silver nanocomposite is dispersed on the surface the substrate, contacting the bacteria or the medium comprising the bacteria with the PMMA/silver nanocomposite membrane on the surface of the substrate may advantageously increase the surface area of the PMMA/silver nanocomposite which interacts with the bacteria and/or from which active antimicrobial substances, e.g. Ag and/or Ag ions, are released into the medium.

By being disposed upon the substrate, the PMMA/silver nanocomposite can be a separately formed membrane formed prior to disposition upon the substrate and then adhered to the surface of the substrate by, for example, gluing, taping, sewing, a silane coupling agent (See U.S. Pat. No. 4,365,359 A, incorporated herein by reference in its entirety), or a mechanical fastening such as a slot and bead (Zip-lock) means. In another embodiment, the PMMA/silver nanocomposite membrane can be formed on the substrate surface by, for example, synthesizing an appropriate amount of the PMMA/silver nanocomposite directly on the surface of the substrate according to the first aspect of the disclosure, electrospraying, or spin-coating to obtain the PMMAJsilver nanocomposite membrane of a desired thickness and coverage of the substrate surface. In still another embodiment, the PMMA/silver nanocomposite membrane may be incorporated into the surface of the substrate, e.g., at least partially embedded within the surface of the substrate.

Like the PMMA/silver nanocomposite alone, the membrane of the PMMA/silver nanocomposite on a substrate may be in contact with a fluid or particulate solid medium comprising the bacteria by batch mixing the PMMA/silver nanocomposite membrane coated substrate with the fluid or the particulate solid medium, preferably under constant agitation (e.g. stirring, shaking, or vortexing).

In other embodiments, the PMMA/silver nanocomposite or the PMMA/silver nanocomposite membrane coated substrate may be in the form of granular particles, which can be installed in a fixed bed reactor or fluidized bed reactor. A fluid medium comprising the bacteria can be applied to a fixed bed column or reactor of the PMMA/silver nanocomposite or the PMMA/silver nanocomposite membrane coated substrate to come into contact with the PMMA/silver nanocomposite, and the effluent of the column or reactor comprises the treated fluid medium in which growth of the bacteria is inhibited.

Alternatively, the PMMA/silver nanocomposite or the PMMA/silver nanocomposite membrane coated substrate can form a fluidized bed reactor with a fluid medium comprising the bacteria, for example, by introducing the pressurized fluid medium, either in a liquid form, or in a gaseous form, or in a mixed liquid and gaseous form, through the particulate medium of the PMMA/silver nanocomposite or the PMMA/silver nanocomposite membrane coated substrate. In the fluidized bed reactor, contact between the PMMA/silver nanocomposite or the PMMA/ silver nanocomposite membrane coated substrate and the fluid medium is greatly enhanced, as compared to that in a fixed bed column or reactor, leading to a higher growth inhibition of the bacteria in the fluid medium.

Figure 5:
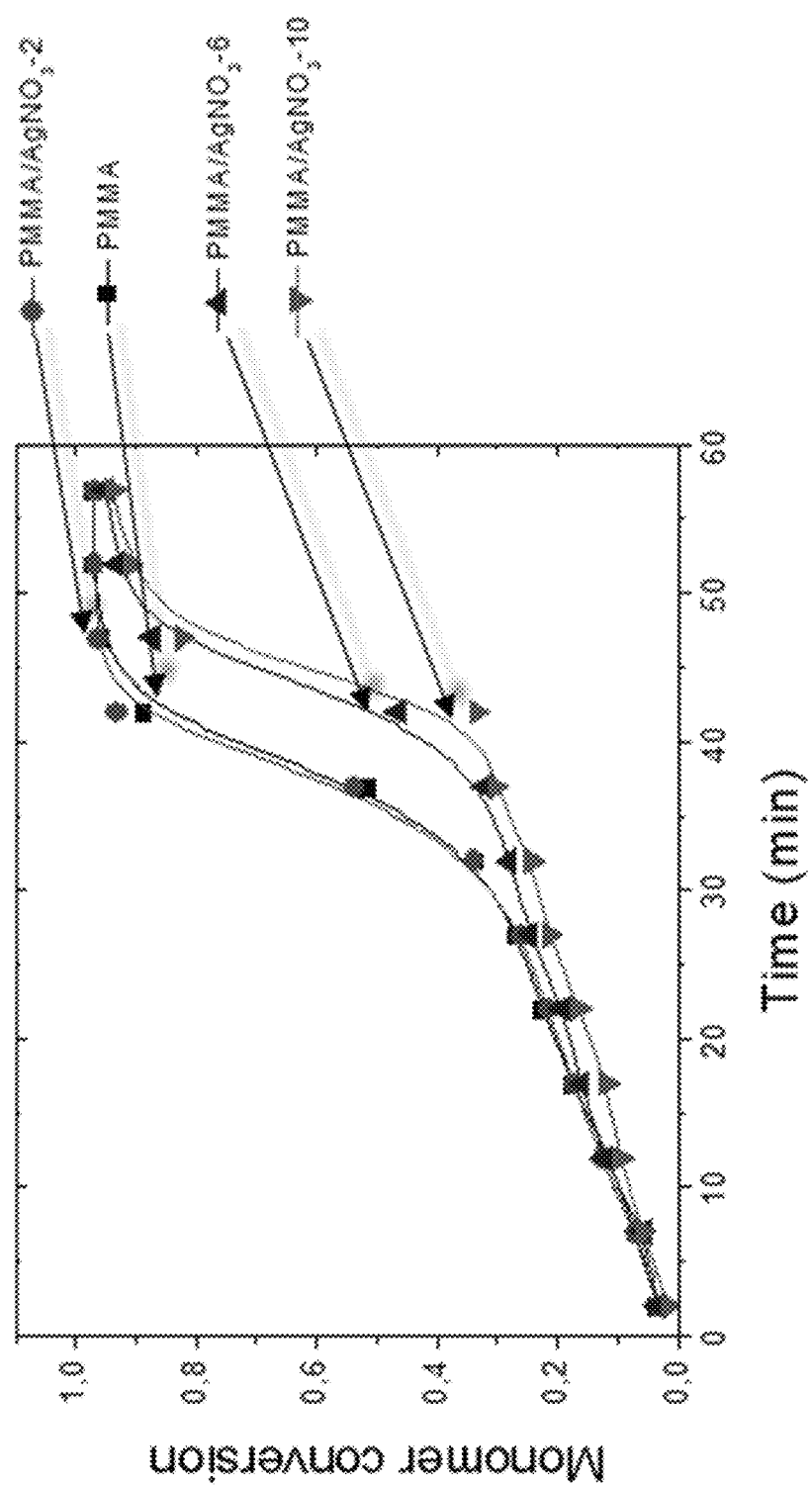
FIG. 5 is a graphical presentation showing the monomer conversion value with time during the synthesis of the neat PMMA and the PMMA/Ag nanocomposites by in situ bulk polymerization in the presence of BPO at an initial concentration of 0.03 mol/L and at 80° C. PMMA, PMMA/$AgNO_3$-2, PMMA/$AgNO_3$-6, and PMMA/$AgNO_3$-10 represent the neat PMMA and the PMMA/silver nanocomposites prepared with 2%, 6%, and 10% by volume relative to the volume of the MMA monomers of 0.1 M $AgNO_3$ dissolved in DMF, respectively.

Whether the contacting of the fluid medium comprising the bacteria with the PMMA/silver nanocomposite or the PMMA/silver nanocomposite membrane coated substrate is effected by batch mixing, and/or fixed or fluidized bed reactor, the fluid medium flow over the PMMA/silver nanocomposite surface is preferably turbulent to improve mixing and mass transfer rates between the bacteria and the antimicrobial agents, such as silver and/or silver ions, released from the PMMA/silver nanocomposite. One way to induce a turbulent fluid medium flow over the PMMA/silver nanocomposite surface is by agitating the fluid medium while it is contacting the PMMA/silver nanocomposite or the PMMA/silver nanocomposite membrane coated substrate. Another way is by providing a geometric configuration of the mass of the PMMA/silver nanocomposite or the PMMA/ silver nanocomposite membrane coated substrate to result in such a turbulent fluid medium flow. An exemplary configuration is a helix axially disposed on a rod as illustrated in FIG. 5 of International Patent Application Publication No. WO2002083570 A1, incorporated herein by reference in its entirety. The purpose of such a geometric configuration or the like is to enhance turbulent flow by creating counter-rotating vortices, cross-current mixing, division and recombination of fluid, and otherwise mixing and agitating the fluid stream.

A mass of the PMMA/silver nanocomposite or the PMMA/silver nanocomposite membrane coated substrate can be pressed, molded, or packaged into a variety of forms to facilitate growth inhibition of the bacteria in the medium and/or removal of the PMMA/silver nanocomposite or the PMMA/silver nanocomposite membrane coated substrate from the bacteria or the treated medium when a desired efficiency of bacterial growth inhibition is attained, and/or when the bacterial growth inhibition capacity of the PMMA/ silver nanocomposite or the PMMA/silver nanocomposite membrane coated substrate is diminished or exhausted. Non-limiting examples of the forms include a granule, a pellet, a sphere, a powder, a woven fabric, a non-woven fabric, a mat, a felt, a block, and a honeycomb.

When the medium comprising the bacteria is a semi-solid, such as an agar, a gel, a cream, a lotion, or a paste, the contacting of the semi-solid medium comprising the bacteria with the PMMA/silver nanocomposite or the PMMA/silver nanocomposite membrane coated substrate may be accomplished by, for example, dispersing the powder, particles, granules, or pellets of the PMMA/silver nanocomposite or the PMMA/silver nanocomposite membrane coated substrate in the semi-solid medium, or applying the powder, particles, granules, pellets, a fabric, or a mat or sheet of the PMMA/silver nanocomposite or the PMMA/silver nanocomposite membrane coated substrate on the surface of the semi-solid medium, such that the PMMA/silver nanocomposite or the PMMA/silver nanocomposite membrane coated substrate can contact the bacteria directly and/or the active antimicrobial substances, such as Ag and/Ag ions, released from the PMMA/silver nanocomposite can diffuse into the semi-solid medium and then reach and contact the bacteria. In some embodiments, the effective amount of the PMMA/silver nanocomposite for inhibiting the bacteria present in a semi-solid medium lies in the range of about 20-400 µg/ml, 30-300 µg/ml, 50-200 µg/ml, 80-150 µg/ml, 100-120 µg/ml semi-solid medium.

When the medium comprising the bacteria is a solid surface, e.g. a bacteria contaminated surface of a medical device, the contacting of the solid surface containing the bacteria with the PMMA/silver nanocomposite may be accomplished by, for example, covering the solid surface with the powder, particles, granules, pellets, a fabric, or a mat or sheet of the PMMA/silver nanocomposite or the PMMA/silver nanocomposite membrane coated substrate.

Regardless of the type of the medium comprising the bacteria, and depending on the temperature sensitivity of the bacteria, the contacting may be performed at a temperature of 4-70° C., 10-60° C., 20-50° C., or 25-40° C., and at a pressure of 0.1-60 bar, 0.5-50 bar, 1-30 bar, or 1-10 bar. The time for the contacting may vary without limitation, depending on, for example, the efficiency of the contacting, the amount and composition, particularly the silver nanoparticle content, of the PMMA/silver nanocomposite, the sensitivity of the bacteria to the PMMA/silver nanocomposite, the initial number of the bacteria, and the desirable growth inhibition efficiency of the bacteria.

Having generally described this invention, a further understanding can be obtained by reference to certain specific examples which are provided herein for purposes of illustration only and are not intended to be limiting unless otherwise specified.

EXAMPLE

1. Materials

Methyl methacrylate (MMA) with a purity ≥99% was purchased from Alfa Aesar, and the hydroquinone inhibitor was removed by passing MMA at least twice through disposable columns packed with inhibitor-removers supplied from Aldrich before any use of the MMA. The free radical initiator, benzoyl peroxide (BPO), with a purity >97% was provided by Alfa Aesar, and purified by fractional recrystallization twice with methanol purchased from Chem-Lab. For the formation of silver nanoparticles, solid silver nitrate ($AgNO_3$) from Mallinckrodt was dissolved in dimethylformamide (DMF) (J.T. Baker). All other chemicals used were of analytical grade and were used as received without further purification.

2. Synthesis of PMMA/Silver Nanocomposites by In-Situ Bulk Radical Polymerization 0.1 M $AgNO_3$ solution in DMF was prepared. An appropriate amount of this solution was dispersed in 12 mL of the MMA monomer in a 100 mL conical flask by adequate magnetic and supersonic agitation. Three different mixtures containing 2, 6 and 10% (v/v) of 0.1 M $AgNO_3$/DMF relative to the MMA monomer were prepared, followed by the addition of BPO as the initiator at the initial concentration of 0.03 M. The resulting reaction mixture was degassed by passing nitrogen into the mixture and used immediately.

In order to study the reaction kinetics, free radical bulk polymerization was carried out in small test-tubes by heating the initial MMA monomer-$AgNO_3$—BPO initiator mixture at 80° C. for a suitable time. According to this technique, 1 mL of the pre-weighted mixtures of the MMA monomer with the BPO initiator and the appropriate amount of the $AgNO_3$/DMF solution were placed into a series of 10 small test-tubes. After degassing with nitrogen, they were sealed and placed into a pre-heated bath at 80° C. Each test-tube was removed from the bath at pre-specified time intervals, and was immediately frozen after the addition of a few drops of hydroquinone in order to stop the reaction. The product was isolated after dissolution in $CH_2Cl_2$ and re-precipitation in MeOH. A different procedure for the nanocomposite isolation was followed in the last 1 or 2 samples of each experiment in the following manner. Since the reaction product of the PMMA/silver nanocomposite was a solid, when the reaction was complete, the test-tubes were broken and the products were obtained. In this way it was ensured that the silver nanoparticles were enclosed in the PMMA polymer matrix. Subsequently, all isolated materials were dried till a constant weight was achieved in a vacuum oven at room temperature. All of the final samples were weighed and the degree of conversion was estimated gravimetrically. The experiments were repeated thrice and the average values are reported. Throughout the polymerization, all solutions were kept in a dark place to avoid any photochemical reactions.

Additionally, the same experiment was repeated except that only the MMA monomer and the BPO initiator were used without adding any $AgNO_3$ to synthesize neat PMMA.

3. X-Ray Diffraction (XRD)

The crystalline structure of the prepared PMMA/Ag nanoparticles was characterized using X-ray diffraction (XRD) in a Rigaku Miniflex II instrument equipped with CuKa generator ($\lambda$=0.1540 nm). The XRD patterns were recorded at a 2θ range of 5-85° and a scan speed of 2° $min^{-1}$.

4. Fourier-Transform Infra-Red (FTIR)

The chemical structures of the neat PMMA and PMMA/Ag nanocomposites were confirmed by recording their IR spectra. The instrument used was a Spectrum 1 spectrophotometer from Perkin Elmer with an attenuated total reflectance (ATR) device. ATR was necessary since the samples with high amounts of Ag nanoparticles were not transparent. Measurements were carried out using thin films prepared in a hot hydraulic press with the spectra recorded over the range from 4000 to 600 $cm^{-1}$ at a resolution of 2 $cm^{-1}$. Thirty-two scans were performed and averaged to reduce noise. Several peaks were identified by the instrument's software.

5. Differential Scanning Calorimetry (DSC)

In order to estimate the glass transition temperature of every sample prepared, the DSC-Diamond (Perkin-Elmer) was used. Approximately 5-6 mg of each sample were weighed, put into the standard Perkin-Elmer sample pan, sealed and placed into an appropriate position of the instrument. Subsequently, the sample was first heated to 180° C. at a rate of 10° C. $min^{-1}$ to ensure complete polymerization of the residual MMA monomer. Then the sample was cooled to 30° C., and its glass transition temperature was measured by heating the sample again to 180° C. at a rate of 20° C. $min^{-1}$. All the results were obtained from the second heating process.

6. Gel Permeation Chromatography (GPC)

The molecular weight distribution (MWD) and the average molecular weights of the neat PMMA and all of the PMMA/silver nanocomposites were determined by GPC. The instrument used was a PL-GPC 50 Plus model from Polymer Laboratories that includes an isocratic pump, a differential refractive index detector, and three PLgel 5µ MIXED-C columns in series. All the samples were dissolved in tetrahydrofuran (THF) at a constant concentration of 1 mg $mL^{-1}$. After filtration, 200 µL of each sample was injected into the chromatograph. The elution solvent was THF at a constant flow rate of 1 mL $min^{-1}$, and the entire system was kept at a constant temperature of 30° C. Calibration of GPC was carried out using standard poly(methyl methacrylate) samples (Polymer Laboratories) with a peak molecular weight ranging from 690 to 1 944 000 and the universal calibration method with appropriate Mark-Houwink constants.

7. Thermogravimetric Analysis (TGA)

The thermal stability of the samples was measured by thermogravimetric analysis. TGA was performed on a Pyris 1 TGA thermal analyzer (Perkin-Elmer) with the samples weighing about 5-8 mg. The samples were heated from ambient temperature to 600° C. at a heating rate of 20° C. min$^{-1}$ under a nitrogen flow.

8. Formation of Silver Nanoparticles

One of the major issues in the synthesis of silver nanoparticles is how to achieve the reduction of Ag$^+$ to Ag$^0$ as well as how to prepare stable particles. In order to meet these demands, a number of reducing agents have been employed. In this investigation, except for a small amount of DMF used as a solvent for AgNO$_3$, no other compound was added to the reaction mixture. Then, it was really interesting to see if reduction of Ag cations indeed happened. FIG. 1 presents the pictures showing: (a) the neat PMMA obtained after the reaction of MMA with BPO at 80° C.; and (b) and (c) the PMMA/silver nanocomposites obtained after the reaction of MMA with BPO at 80° C. in the presence of 2% or 6% by volume relative to the volume of the MMA monomers of 0.1 M AgNO$_3$ dissolved in DMF. From the pictures it was clear that while the neat PMMA produced was almost transparent and colorless, the PMMA/silver composites had a color from golden yellow to pale brown. The color observed is characteristic of the reduction of silver ions into Ag nanoparticles of zero valence. The question then arises on how this was achieved. Referring to FIG. 2, in order to provide an explanation, we turned to free radical polymerization of MMA known to include the main reaction steps of initiation, propagation and termination. Propagation, which is depicted in Reaction (1) of FIG. 2, refers to a reaction of a macro-radical with a monomer molecule in order to increase the length of the radical by the addition of the monomer. Reaction (2) of FIG. 2 depicts a reaction of chain transfer to monomer (CTM), which takes place during MMA polymerization and is competitive to the propagation, ( ). In Reactions (1) and (2), the reactants are exactly the same, but the products are different. In CTM, transfer of a β-hydrogen from the macro-radical to the monomer molecule usually takes place. Thus, the macro-radical stops to exist, forming a macromolecule with a terminal double bond, while a new radical starts at the monomer molecule. As depicted in Reaction (3) of FIG. 2, we can assume that instantaneously a hydrogen radical is formed. As depicted in Reaction (4) FIG. 2, the Ag$^+$ cations formed from the dissociation of AgNO$_3$ disperse in PMMA and coordinate to the oxygen atoms of the carbonyl functional groups of PMMA. This is a reasonable explanation and has been reported previously in the literature for the acrylate in PMMA (See Kassaee, M. Z., Mohammadkhani, M., Akhavan, A., Mohammadi, R. In situ formation of silver nanoparticles in PMMA via reduction of silver ions by butylated hydroxytoluene. Struct. Chem. 22, 11-15 (2011), incorporated herein by reference in its entirety). Referring to Reaction (5) of FIG. 2, the reduction of Ag$^+$ to atomic silver can be achieved by the hydrogen radicals formed from the CTM reaction. Finally, silver produced aggregates to form Ag nanoparticles in PMMA as shown in Reaction (6) of FIG. 2. In the PMMA/silver nanocomposite, the PMMA prevents precipitation and further aggregation of the silver nanoparticles, and stabilizes and protects the silver nanoparticles with its carboxylate functional groups.

9. Characterization of the PMMA/Silver Nanocomposites

Figure 3:
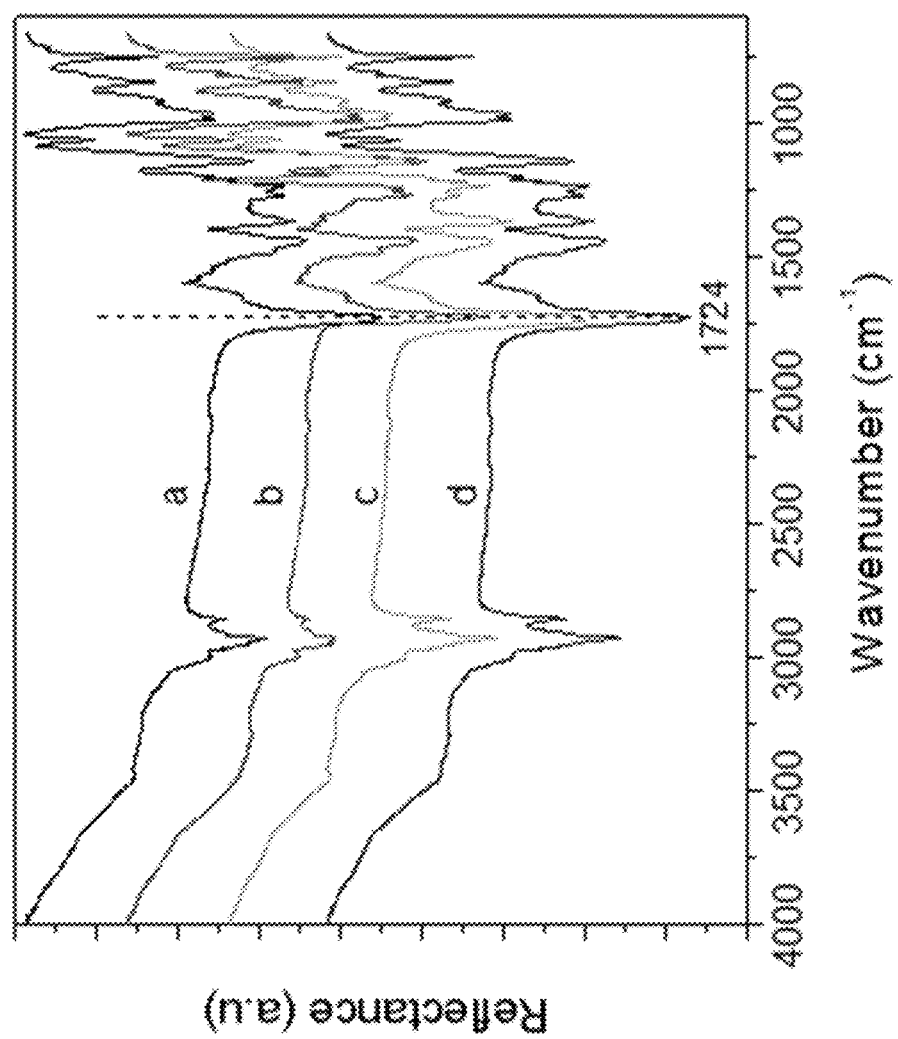
FIG. 3 is a graphical presentation of the FTIR spectra of the neat PMMA represented by line (a), and the PMMA/silver nanocomposites prepared with 2%, 6%, and 10% by volume relative to the volume of the MMA monomers of 0.1 M $AgNO_3$ dissolved in DMF represented by lines (b), (c), and (d), respectively.

Possible physicochemical interactions between the silver nanoparticles and the PMMA matrix in the PMMA/silver nanocomposites were tested using FTIR-ATR measurements. FIG. 3 shows the FTIR spectra of the neat PMMA and the PMMA/silver nanocomposites prepared. The spectra of the neat PMMA and all the PMMA/silver nanocomposites displayed a sharp peak at 1724 cm$^{-1}$ corresponding to the carbonyl bond (C=O) stretching vibrations. Two small peaks at 3000/2940 cm$^{-1}$ are attributed to methyl ester C—H stretching vibrations. An additional small peak at 2855 cm$^{-1}$ is due to —CH$_3$ stretching vibrations. The peaks at 1436/1482 cm$^{-1}$ correspond to C—H deformations. The peak at 1365 cm$^{-1}$ correspond to —CH$_3$ symmetrical deformation. Finally, the peaks at 1271/1233/1143/985 cm$^{-1}$ are attributed to C—O stretching. Similar reflectance bands have been observed in FTIR-ATR for pure PMMA in the literature. See Penescu, M. Diffusion of cyclic versus linear poly(oxyethylene) oligomers in poly(methyl methacrylate) by ATR-FTIR spectroscopy, Ph.D. Thesis, Georgia Institute of Technology, 2009, incorporated herein by reference in its entirety. Moreover, the spectra of the neat PMMA and all the PMMA/silver nanocomposites looked similar, indicating that the inclusion of the silver nanoparticles in the PMMA polymer matrix is of a physical interaction without a strong chemical bond.

Figure 4:
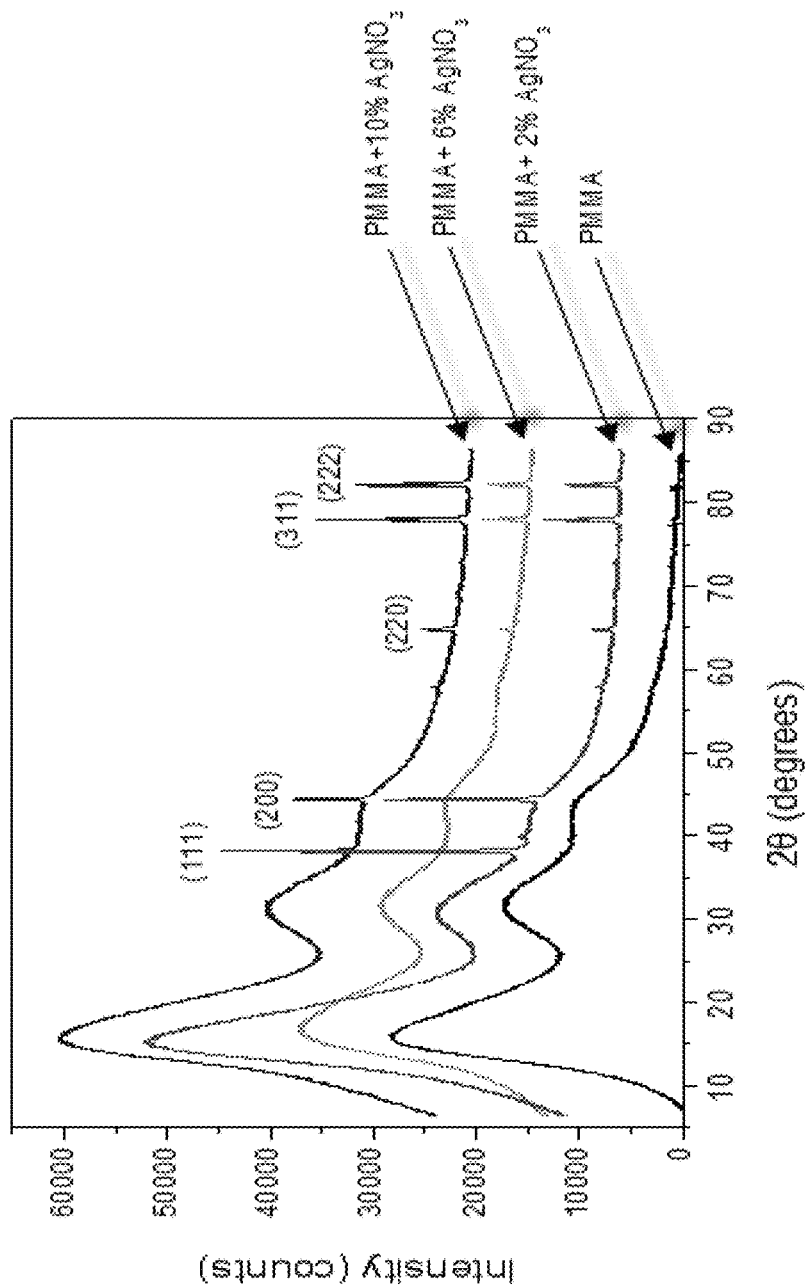
FIG. 4 is a graphical presentation of the X-Ray diffraction (XRD) patterns of the neat PMMA and the PMMA/silver nanocomposites prepared with 2%, 6%, and 10% by volume relative to the volume of the MMA monomers of 0.1 M $AgNO_3$ dissolved in DMF. PMMA, PMMA+2% $AgNO_3$, PMMA+6% $AgNO_3$, and PMMA+10% $AgNO_3$ represent the neat PMMA and the PMMA/silver nanocomposites prepared with 2%, 6%, and 10% by volume relative to the volume of the MMA monomers of 0.1 M $AgNO_3$ dissolved in DMF, respectively.

FIG. 4 shows the XRD patterns of the neat PMMA and the PMMA/silver nanocomposites recorded in the 2θ angle range of 5°-85°. The XRD pattern of the neat PMMA displays three very broad peaks at the 2θ angle of 16°, 32° and 43°, indicating the amorphous structure of the polymer. With the PMMA/Ag nanocomposites where the Ag nanoparticles were formed in the PMMA polymer matrix, the XRD patterns displayed 5 additional sharp peaks at 2θ values of 38.2, 44.4, 64.7, 77.7 and 82.0° corresponding to the (111), (200), (220), (311) and (222) crystalline planes of the face-centered cubic silver, respectively, indicating the formation of the silver crystalline structure.

The average particle size of the silver nanoparticles in the PMMA/silver nanocomposites can be calculated using Debye-Scherrer equation:

$$n = \frac{K\lambda}{\beta\cos\theta} \quad (1)$$

where K is the Scherrer constant with value from 0.9 to 1 (shape factor), λ is the X-ray wavelength (1.5418 Å), $\beta_{1/2}$ is the width of the XRD peak at half height and θ is the Bragg angle.

Using the above Scherrer's equation and considering the dominant peak at 38.2°, the average particle size of the silver nanoparticles was calculated to be around 41-42 nm in all three PMMA/Ag nanocomposites. It seems that the average particle size did not vary with the amount of silver. These silver nanoparticle average particle size values are somehow higher than the values reported in the literature (around 30 nm) (See Penescu, M. Diffusion of cyclic versus linear poly(oxyethylene) oligomers in poly(methyl methacrylate) by ATR-FTIR spectroscopy, Ph.D. Thesis, Georgia Institute of Technology, 2009, incorporated herein by reference in its entirety), and it may be explained by the fact that no additional reducing agent was added into the reaction mixture for the reduction of silver ion to form the silver nanoparticles.

10. Polymerization Kinetics

FIG. 5 shows the MMA monomer conversion with time measured gravimetrically for the neat PMMA and the PMMA/Ag nanocomposites. The conversion curves indicate that all of the polymerizations exhibit a behavior typical of poly(methyl methacrylate) with a strong gel-effect starting at a low conversion (i.e. near 30%). The key points of the phenomena taking place are briefly discussed next. In the first stage of polymerization with low conversions, the conversion vs time curve follows the 'classical' free-radical kinetics that has an almost linear relationship between conversion X, or more precisely −ln(1−X) with time, indicating a purely chemical control of the polymerization. See Achilias D S. A review of modeling of diffusion controlled polymerization reactions, Macromol Theory Simul 2007; 16: 319-47, incorporated herein by reference in its entirety. After a certain conversion value in the region of 20-30% is reached, an increase in the reaction rate takes place followed by an increase in the conversion values. This is the well-known auto-acceleration or gel-effect attributed to the effect of diffusion-controlled phenomena on the termination reaction and to the reduced mobility of live macro-radicals that limits termination collisions. Therefore, the radical concentration increases locally, leading to increased reaction rates. See Verros G D, Achilias D S. Modeling gel-effect in branched polymer systems: Free-radical solution homopolymerization of Vinyl Acetate. J Appl Polym Sci 2009; 111: 2171-2185; and Achilias D S, Verros G V. Modeling of diffusion-controlled reactions in free-radical solution and bulk polymerization: Model Validation by DSC experiments. J Appl Polym Sci. 2010; 116: 1842-56, each incorporated herein by reference in its entirety. Afterwards, the reaction rate falls significantly and the curvature of the conversion versus time curve changes. At this conversion stage from approximately 50% to 80% conversion, the observed decrease in the termination reaction rate is not so abrupt but only gradual. At this stage, the center-of-mass motion of radical chains becomes very slow and any movement of the growing radical site is attributed to the addition of monomer molecules at the chain end. This additional diffusion mechanism is the so-called 'reaction diffusion'. The higher is the propagation reaction rate value, the more likely the reaction diffusion is rate determining. Finally, at very high conversions, beyond 90%, the reaction rate tends asymptotically to zero and the reaction almost stops before the full consumption of the monomer. Thus a glassy state appears, and it corresponds to the well-known glass-effect attributed to the effect of diffusion-controlled phenomena on the propagation reaction and the reduced mobility of monomer molecules to find a macro-radical and react (See Achilias D S. A review of modeling of diffusion controlled polymerization reactions Macromol Theory Simul 2007; 16: 319-47; Verros G D, Achilias D S. Modeling gel-effect in branched polymer systems: Free-radical solution homopolymerization of Vinyl Acetate. J Appl Polym Sci 2009; 111: 2171-2185; Achilias D S, Verros G V. Modeling of diffusion-controlled reactions in free-radical solution and bulk polymerization: Model Validation by DSC experiments. J Appl Polym Sci. 2010; 116: 1842-56; each incorporated herein by reference in its entirety).

It has been reported that the presence of nanoparticles may influence polymerization kinetics, especially for monomers exhibiting a strong effect of diffusion phenomena on the reaction kinetics. See Achilias D S, Nikolaidis A K, Karayannidis G P. PMMA/organomodified montmorillonite nanocomposites prepared by in situ bulk polymerization: study of the reaction kinetics. J Therm Anal Calorim 2010; 102(2): 451-460, incorporated herein by reference in its entirety. These results were attributed to the decreased free-volume of the reaction mixture as well as to the restriction imposed on the diffusion of macro-radicals in space due to the existence of the organic modifiers in the MMT platelets. Therefore, the OMMT platelets with the large chemical structure of the modifiers add an extra hindrance in the movement of the macro-radicals in space in order to find one another and react (terminate), resulting in locally increased radical concentrations.

According to these experimental data, it appears that the presence or the formation of silver nanoparticles during the reaction has two effects on the polymerization kinetics. Referring to FIG. 5, as the amount of $AgNO_3$ increases, the initial rate (slope of the conversion vs time curve) is slightly reduced followed by a clear reduction in the conversion values at which the gel-effect was observed. The first has to do with pure chemical reaction kinetics, while the second relates to the effect on the diffusion-controlled phenomena. In order to explain the effect of Ag NPs on the initial polymerization kinetics, some basics of radical polymerization are presented below. Thus, the polymerization rate, represented by the variation of monomer conversion (X) with time (t), is expressed by the following equation, assuming the steady-state approximation for the total radical population, which has been proven to hold at low conversion values (See Achilias D S. A review of modeling of diffusion controlled polymerization reactions Macromol Theory Simul 2007; 16: 319-47, incorporated herein by reference in its entirety).

$$\frac{dX}{dt} = (k_p + k_{trM})\left(\frac{fk_d[I]}{k_t}\right)^{1/2}(1-X) \qquad (2)$$

Where $k_p$, $k_{trM}$, $k_t$ and $k_d$ denote the kinetic rate constants of the propagation, chain transfer to monomer, termination and initiator decomposition reactions, f is the initiator efficiency, and [I] is the initiator concentration.

Assuming that the initiator concentration remains almost constant at early reaction times and all kinetic rate constants are independent of conversion, equation (2) can be integrated to give rise to:

$$-\ln(1-X) = k_{eff} t \qquad (3)$$

where $$k_{eff} = (k_p + k_{trM})\left(\frac{fk_d[I]_0}{k_t}\right)^{1/2} \qquad (4)$$

Figure 6:
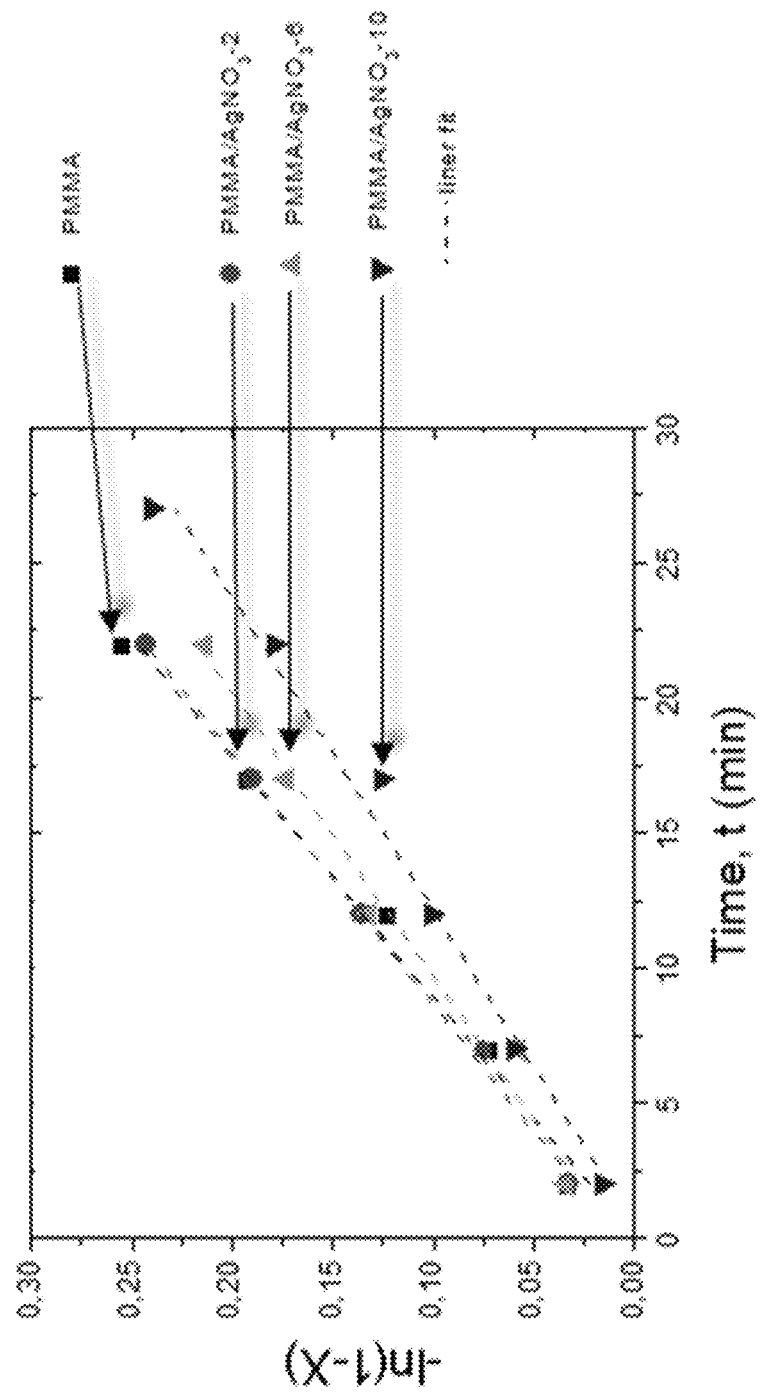
FIG. 6 is a graphical presentation of the linear relationship between $-\ln(1-X)$ and time (t) for the neat PMMA and the PMMA/silver nanocomposites, with the slope for the linear fit being the estimate of the effective rate constant ($K_{eff}$) for the bulk polymerization of MMA in the presence of BPO at an initial concentration of 0.03 M and at 80° C. to form the neat PMMA and the PMMA/silver nanocomposites containing different amounts of silver nanoparticles. X: monomer conversion. PMMA, PMMA/$AgNO_3$-2, PMMA/$AgNO_3$-6, and PMMA/$AgNO_3$-10 represent the neat PMMA and the PMMA/silver nanocomposites prepared with 2%, 6%, and 10% by volume relative to the volume of the MMA monomers of 0.1 M $AgNO_3$ dissolved in DMF, respectively.

By plotting the left-hand side of eq. (3) (i.e. −ln(1−X)) versus time (t) at low conversions, straight lines should appear having a slope equal to the effective rate constant $k_{eff}$. Such results for the neat PMMA and the PMMA/Ag nanocomposites with different amounts of the Ag nanoparticles are presented in FIG. 6 using the experimental data in the conversion range of 1-24%. From the slope of the linear fit in FIG. 6, the following values of the effective rate constant were obtained: $112.6 \times 10^{-4} \pm 6.9 \times 10^{-4}$, $107.1 \times 10^{-4} \pm 3.1 \times 10^{-4}$, $95 \times 10^{-4} \pm 7.9 \times 10^{-4}$, $86.1 \times 10^{-4} \pm 5.3 \times 10^{-4}$ min$^{-1}$ for the neat PMMA and PMMA/$AgNO_3$-2%, 6%, and 10%, respectively. The corresponding correlation coefficients ($R^2$) were 0.9853, 0.9967, 0.9729, and 0.9812. Thus, $k_{eff}$ is lower for the PMMA/Ag nanocomposites than that for the neat PMMA, and $k_{eff}$ reduces continuously as the amount of the silver nanoparticles in the PMMA/Ag nanocomposite increases.

Figure 7:
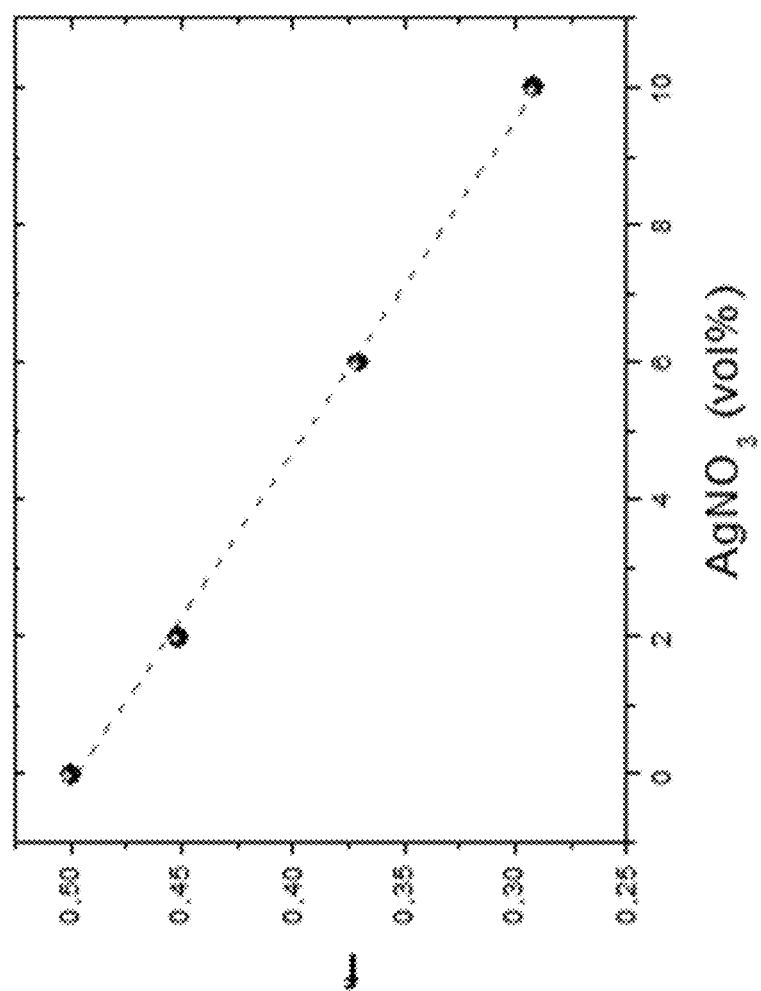
FIG. 7 is a graphical presentation showing the linear relationship between the estimated initiator efficiency f and the different amounts of 0.1 M $AgNO_3$ expressed in % volume relative to the volume of the MMA monomers for the preparation of the PMMA/silver nanocomposites.

The effective rate constant of PMMA can be evaluated from available literature data on the kinetic rate constant at low conversions. A number of different values have been proposed, for example, one by Zoller et al. (See Zoller, A., Gigmes, D., Guillaneuf, Y in their paper "Simulation of "cold" free radical polymerization of methyl methacrylate using a tertiary amine/BPO initiating system," Polymer Chemistry, 2015 Advance article DOI: 10.1039/C5PY00229J, incorporated herein by reference in its entirety). The authors of the paper proposed the following values: $k_p=2.67\times10^6*\exp(-22360/RT)$, $k_t=1.984\times10^8*\exp(-5890/RT)$ L/mol/s, $k_d=5\times10^{16}*\exp(-143000/RT)$ s$^{-1}$, $k_{trM}=5\times10^{-5}*k_p$, while for f different values have been proposed in the literature. When f is selected to be 0.5 and the temperature is set to be 80° C., at which temperature the experiments of this study were carried out, the values of the above kinetic rate constants are: $k_p=1314$ L/mol/s, $k_t=2.668\times10^7$ L/mol/s, $k_d=3.5\times10^{-5}$ s$^{-1}$, $k_{trM}=0.066$ L/mol/s. Using these values and $[I]_0=0.03$ mol/L, the theoretical value of the effective rate constant becomes $k_{eff}=1.84\times10^{-4}$ s-1 or $110.6\times10^{-4}$ min$^{-1}$. This value is very close to the experimentally observed value of $112.6\times10^{-4}$ min$^{-1}$, confirming our experimental data. The next step was to identify which kinetic parameter was affected by the addition of AgNO$_3$. From equation (2), it is unlikely that $k_p$, $k_{trM}$, $k_t$, or $k_d$ may change by the existence of the Ag nanoparticles. Rather, it seems that the initiator efficiency f could be affected. In order to test this assumption, equation (2) was used again by setting f=0.5 only for the neat PMMA and estimating the f values for the PMMA/Ag nanocomposites based on the experimentally measured values of the overall effective rate constant $k_{eff}$. Referring to FIG. 7, when the values of f thus obtained were plotted as a function of the amount of the initially added AgNO$_3$, there was a very good linear relationship between the two variables with the R$^2$ of 0.9981. The results indicate that Ag$^+$ interacts with some of the primary radicals formed from the decomposition of the initiator, resulting in a decreased amount of effective primary radicals capable of reacting with the monomer molecules to initiate polymerization.

Referring to FIG. 5 for the gel-effect region of the conversion vs time profile, the auto-acceleration starts at later reaction times as the amount of Ag$^+$ added increases. This is a direct result of the lower initial slope of the conversion versus time profile explained previously (i.e. since the abrupt increase in conversion starts at approximately 30% conversion, this value is obtained at a later reaction time as the amount of silver increases). In addition, it is observed that the final conversion values for the PMMA/Ag nanocomposites are slightly lower compared to that for the neat PMMA. This could be attributed to the hindered movement of small molecules in the reaction mixture (i.e. monomer molecules or primary initiator radicals) to find a macro-radical and react due to the existence of the Ag nanoparticles as shown in equation 6 of FIG. 2, resulting in larger amounts of unreacted monomer molecules.

Figure 8:
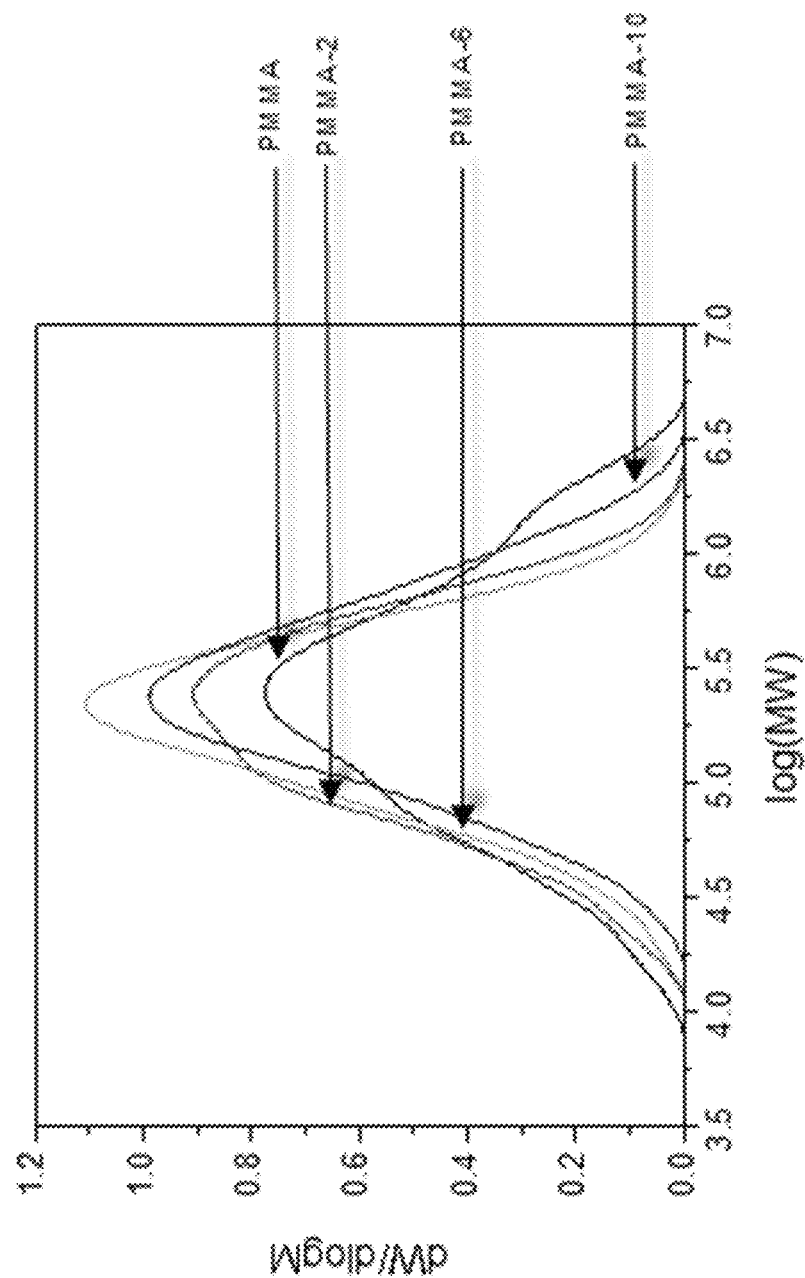
FIG. 8 is a graphical presentation of the gel permeation chromatography (GPC) results showing full molecular weight distribution of the neat PMMA and the PMMA/silver nanocomposites. PMMA, PMMA-2, PMMA-6, and PMMA-10 represent the neat PMMA and the PMMA/silver composites prepared with 2%, 6%, and 10% by volume relative to the volume of the MMA monomers of 0.1 M $AgNO_3$ dissolved in DMF, respectively.

In order to better explain these results, the average molecular weights of all of the PMMA/Ag nanocomposites prepared and their full molecular weight distributions were measured with gel permeation chromatography (GPC), with the results presented in FIG. 8 and Table 1. Referring to Table 1, the number average molecular weight (M$_n$) increases with the increasing amounts of Ag$^+$ added to the reaction mixture, while the weight average molecular weight (M$_w$) tends to decrease with the increasing amounts of Ag$^+$ added to the reaction mixture. Referring to FIG. 8, it seems that the PMMA/Ag nanocomposites with slightly higher number average molecular weights relative to the neat PMMA were produced, but they had a narrower molecular weight distribution (MWD). In order to explain these observations, we turned again to classical free radical polymerization kinetics. Accordingly, the number average molecular weight of a polymer is given by its average degree of polymerization which in turn is calculated from the average kinetic chain length v. This is given by the following equation:

$$\frac{1}{v} = \frac{k_t[P^*]}{k_p[M]} + \frac{k_{trM}[M]}{k_p[M]} = \frac{(fk_d[I]k_t)^{1/2}}{k_p[M]} + C_M \quad (5)$$

From this equation, it is clear that a decreased initiator efficiency f results in increased v and consequently a higher number average molecular weight. A lower number of primary initiator radicals results in macro-radicals with higher chain length. Moreover, the lower final conversion caused by the presence of higher amounts of Ag nanoparticles results in not letting the polymer to increase its high molecular weight tail to higher values. This reduces the polydispersity of the MWD.

TABLE 1

Number-average and weight-average molecular weights (M$_n$ and M$_w$), polydispersity (PD) of the molecular weight distribution (MWD), and glass transition temperature (T$_g$) of the neat PMMA and the PMMA/Ag nanocomposites prepared with various amounts of AgNO$_3$.

|  | M$_n$ | M$_w$ | M$_z$ | PD | Tg |
|---|---|---|---|---|---|
| PMMA | 114570 | 427250 | 1121690 | 3.73 | 98 |
| PMMA/AgNO$_3$-2 | 120035 | 279810 | 528740 | 2.33 | 95 |
| PMMA/AgNO$_3$-6 | 130695 | 288830 | 572750 | 2.21 | 82 |
| PMMA/AgNO$_3$-10 | 164820 | 370620 | 734560 | 2.25 | 80 |

Figure 9:
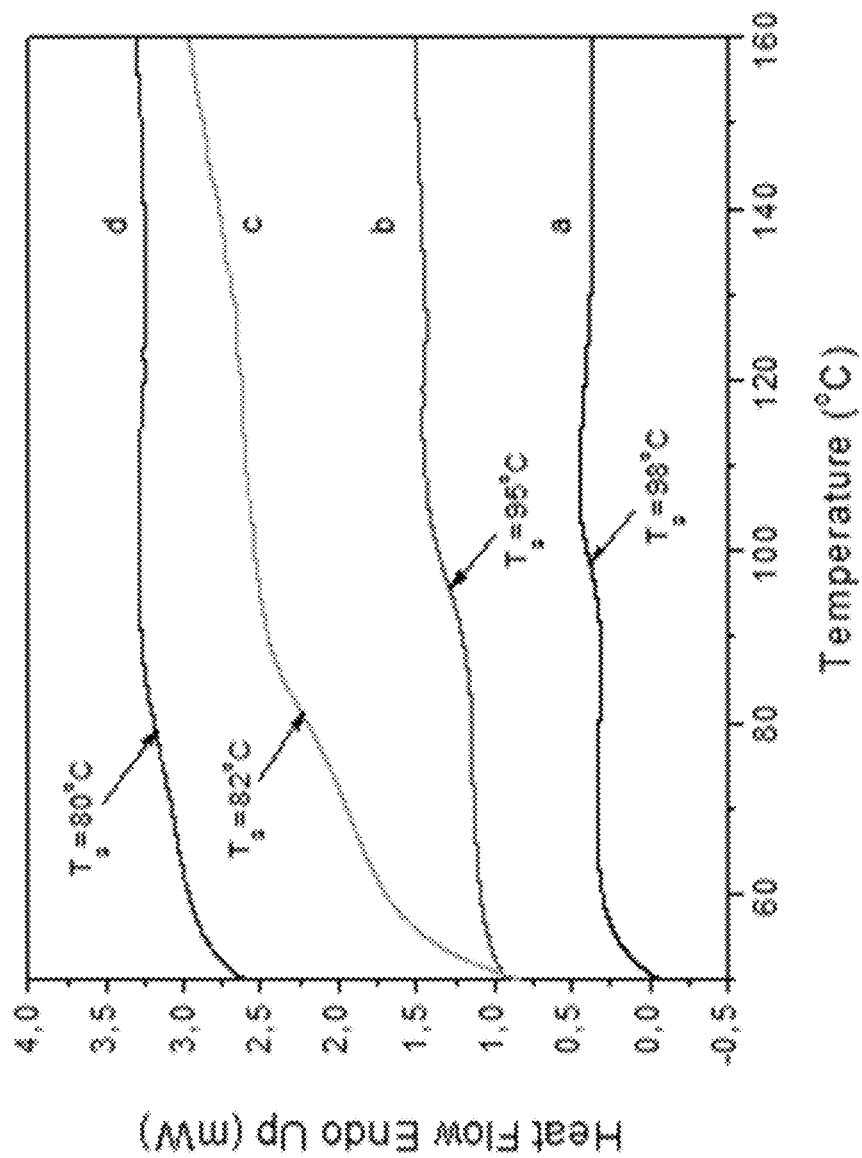
FIG. 9 is a graphical presentation of the differential scanning calorimetry (DSC). traces showing the estimated glass transition temperatures of PMMA on line (a), PMMA/$AgNO_3$-2 on line (b), PMMA/$AgNO_3$-6 on line (c), and PMMA/$AgNO_3$-10 on line (d). PMMA, PMMA/$AgNO_3$-2, PMMA/$AgNO_3$-6, and PMMA/$AgNO_3$-10 represent the neat PMMA and the PMMA/silver composites prepared with 2%, 6%, and 10% by volume relative to the volume of the MMA monomers of 0.1 M $AgNO_3$ dissolved in DMF, respectively. Endo up—the endotherm is recorded in the up direction.

Furthermore, the glass transition temperatures (T$_g$) of the neat PMMA and the PMMA/Ag nanocomposites were determined using DSC according to the procedure described above, with the results showing the amount of heat flow versus temperature presented in FIG. 9. T$_g$ was estimated using the half Cp extrapolation method (See D. S. Achilias, P. Siafaka, A. K. Nikolaidis. Polymerization kinetics and thermal properties of poly(alkyl methacrylate)/organomodified montmorillonite nanocomposite, *Polym. Int.;* 61: 1510-1518 (2012), incorporated herein by reference in its entirety). No DSC artifacts were observed and the results were reproducible. All the T$_g$ values are given in Table 1. The value measured for the neat PMMA (i.e. 98° C.) is close to that reported in the literature, which is usually near 100° C. (See D. S. Achilias, P. Siafaka, A. K. Nikolaidis. Polymerization kinetics and thermal properties of poly(alkyl methacrylate)/organomodified montmorillonite nanocomposite, *Polym. Int.;* 61: 1510-1518 (2012), incorporated herein by reference in its entirety). The T$_g$ value of the PMMA/Ag nanocomposite tends to decrease with an increasing silver content, consistent with the findings by others reported in the literature (See Vodnik, V. V., Bozanic, D. K., Dzunuzovic, E., Vukovic, J. Nedeljkovic, J. M. Thermal and optical properties of silver-poly(methyl methacrylate) nanocomposites prepared by in-situ radical polymerization. Eur. Polym. J. 46, 137-144 (2010), incorporated herein by reference in its entirety), and probably due to the decreased restricted segmental chain mobility of the PMMA anchored to the particles surface. The interaction of polymer chains with nanoparticles surface can alter the chain kinetics by either decreasing or increasing the glass transition temperature of the polymer. The decrease of the T$_g$ values can be explained in terms of the thin film model. When the inter-particles distance is small enough, then the polymer between two particles can be considered as a thin film. Assuming that small or no interfacial interaction between the filler and matrix exists, the $T_g$ decreases as the film thickness, i.e. inter-particles distance decreases.

Figure 10A:
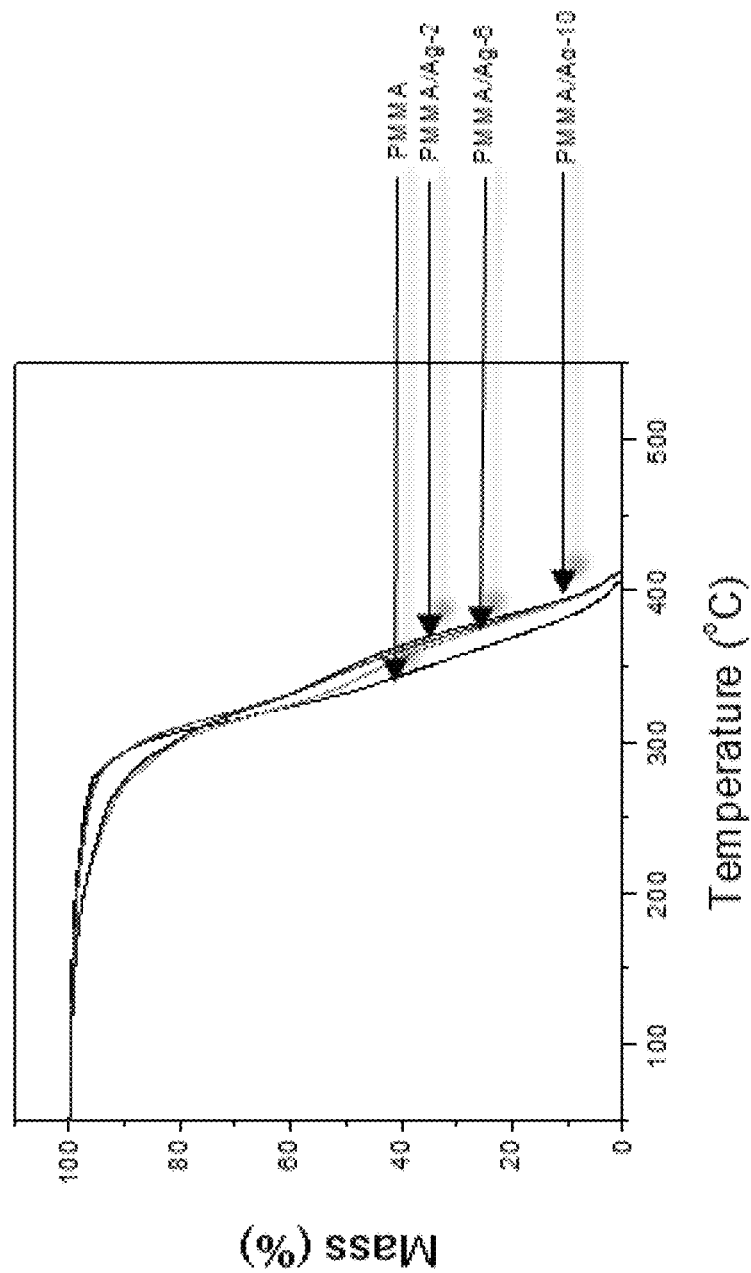
FIG. 10A is a graphical presentation of the thermogravimetric analysis (TGA) results showing the relationship of the mass of the neat PMMA and the PMMA/silver nanocomposites with temperature. PMMA, PMMA/Ag-2, PMMA/Ag-6, and PMMA/Ag-10 represent the neat PMMA and the PMMA/silver nanocomposites prepared with 2%, 6%, and 10% by volume relative to the volume of the MMA monomers of 0.1 M $AgNO_3$ dissolved in DMF, respectively.
Figure 10B:
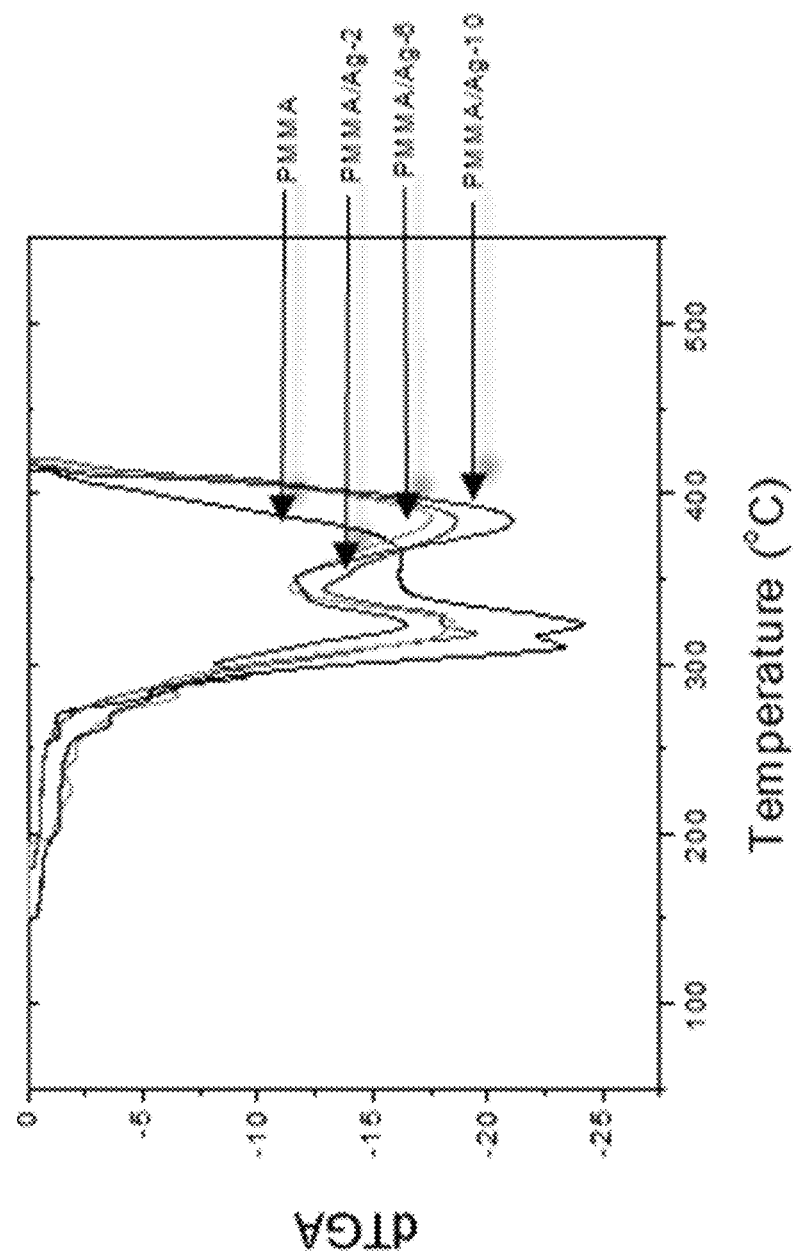
FIG. 10B is a graphical presentation of the differential thermogravimetric curves showing the rate of mass loss as a function of temperature for the neat PMMA and the PMMA/silver nanocomposites. PMMA, PMMA/Ag-2, PMMA/Ag-6, and PMMA/Ag-10 represent the neat PMMA and the PMMA/silver nanocomposites prepared with 2%, 6%, and 10% by volume relative to the volume of the MMA monomers of 0.1 M $AgNO_3$ dissolved in DMF, respectively.

Finally, the thermal stability of the neat PMMA and the PMMA/Ag nanocomposites was examined by thermogravimetric analysis (TGA) in nitrogen atmosphere. Results on the mass and the rate of mass loss as a function of temperature for the neat PMMA and the PMMA/Ag nanocomposites prepared with different amounts of $AgNO_3$ are shown in FIGS. 10A and 10B, respectively. The thermal degradation of radically prepared PMMA has been a subject of numerous studies and usually involves multiple steps assigned to: presence of weak head-to-head linkages, scission of unsaturated terminal groups and random scission of the carbon-carbon main chain. It is generally considered that most of PMMA thermally degrades through depolymerisation, and therefore the kinetics of mass loss are determined by the mode of degradation initiation.

Referring to FIG. 10A, the neat PMMA and PMMA/Ag-2 started to degrade at almost 280° C., while PMMA/Ag-6 and PMMA/Ag-10 started to degrade at a lower temperature near 220° C. The lower degradation start temperature for PMMA/Ag-6 and PMMA/Ag-10 is attributed to the existence of some amount of unreacted monomer (as it was observed from kinetic measurements) which may be evaporated at these temperatures. Referring to FIG. 10B, two groups of distinct peaks were observed. The first group of peaks at 320° C. from the neat PMMA and all of the PMMA/Ag nanocomposites is attributed to the degradation of weak links inside the macromolecular chain or at its end. The second group of peaks at 365-385° C. only from the PMMA/Ag nanocomposites is attributed to random chain scission. Therefore, incorporation of the silver nanoparticles into PMMA shifts the main degradation step to higher temperatures, resulting in protection of the PMMA/Ag nanocomposites from thermal degradation. Another interesting observation is that the neat PMMA has the largest area of the first peak followed by, in descending order, PMMA/Ag-2, PMMA/Ag-6, and PMMA/Ag-10, whereas PMMA/Ag-10 has the largest area of the second peak followed by PMMA/Ag-2 and PMMA/Ag-6, with the neat PMMA not having a discernible second peak. This means that the incorporation of the Ag NPs in the polymer matrix results in a decrease in the defect structures and in production of macromolecules with more uniform chain characteristics. This is in accordance with the results obtained by GPC that the polydispersity of the MWD decreased with the addition of the silver nanoparticles.

11. Antimicrobial Properties of the PMMA/Ag Nanocomposites

The antimicrobial and particularly antibacterial efficiency of the PMMA/Ag nanocomposites produced was estimated by their ability to inhibit the growth of several microorganisms. Four different bacterial strains were used: *Bacillus cereus* (Gram-positive), *Bacillus subtilis* (Gram-positive), *Escherichia coli* (Gram-negative), and *Staphylococcus aureus* (Gram-positive). Bacterial growth was performed in LB while the screening for antibacterial activity was performed using the method of progressive dilution in MMS that contained 150, 125, 100, 75, 50, 25 and 12.5 µg/mL of PMMA or each of the PMMA/Ag nanocomposites. The concentration of the microorganisms in the cultivation medium was $10^5$-$10^6$ CFU/mL.

In brief, a bacteria pre-culture was incubated in Luria Brettani (LB) broth solution at 37° C. with agitation. Thereafter, test samples were set up by grafting 1% by volume relative to the volume of MMS of the resulting full growth bacterial culture into 2 mL of MMS, to which the neat PMMA or individual PMMA/Ag nanocomposites at the amounts of 300, 250, 200, 150, 100, 50 and 25 µg were added. The mixtures were incubated at 37° C. for 24 h, and the optical density (O.D.) at 600 nm of the resulting bacterial cultures was measured using a spectrophotometer (Helios γ, Thermo Electron Corporation, USA). The control sample, which was a bacterial culture obtained in the same fashion except for the addition of any of the polymer materials (i.e. the neat PMMA or the PMMA/Ag NPs nanocomposite), was also included in the study. The % growth was calculated by dividing the measured O.D. of the test sample by that of the control sample. The experiments were carried out in triplicates and the average values are reported.

The effect of the concentration of the neat PMMA and particularly the PMMA/Ag nanocomposites, and the effect of the amount of the Ag nanoparticles incorporated into the PMMA matrix, on the % growth of the test sample bacterial cultures of *Bacillus cereus, Bacillus subtilis, Escherichia coli*, and *Staphylococcus aureus* are presented in FIGS. 11A-11D. The percentage growth of the bacteria decreased with increasing concentrations of the individual PMMA/Ag nanocomposites. At any one of the concentrations tested, particularly greater than 100 µg/2 mL, the PMMA/Ag nanocomposite containing a higher amount of silver displayed a higher antibacterial activity against all of the bacteria tested, with PMMA+10% $AgNO_3$ having a better antimicrobial activity than PMMA+2% $AgNO_3$ and PMMA+6% $AgNO_3$. It should be noted that, since the actual amounts of Ag in the PMMA/Ag nanocomposites were rather low, more specifically 0.023, 0.069 and 0.114 wt % for PMMA+2%, 6% and 10% $AgNO_3$, respectively, the PMMA/Ag nanocomposites may be advantageously used in commercial applications at a low material cost. However, the % growth of the bacteria never reached zero that signifies a complete growth inhibition when using any one of the PMMA/Ag nanocomposites at any of the concentrations tested.

Figure 11A:
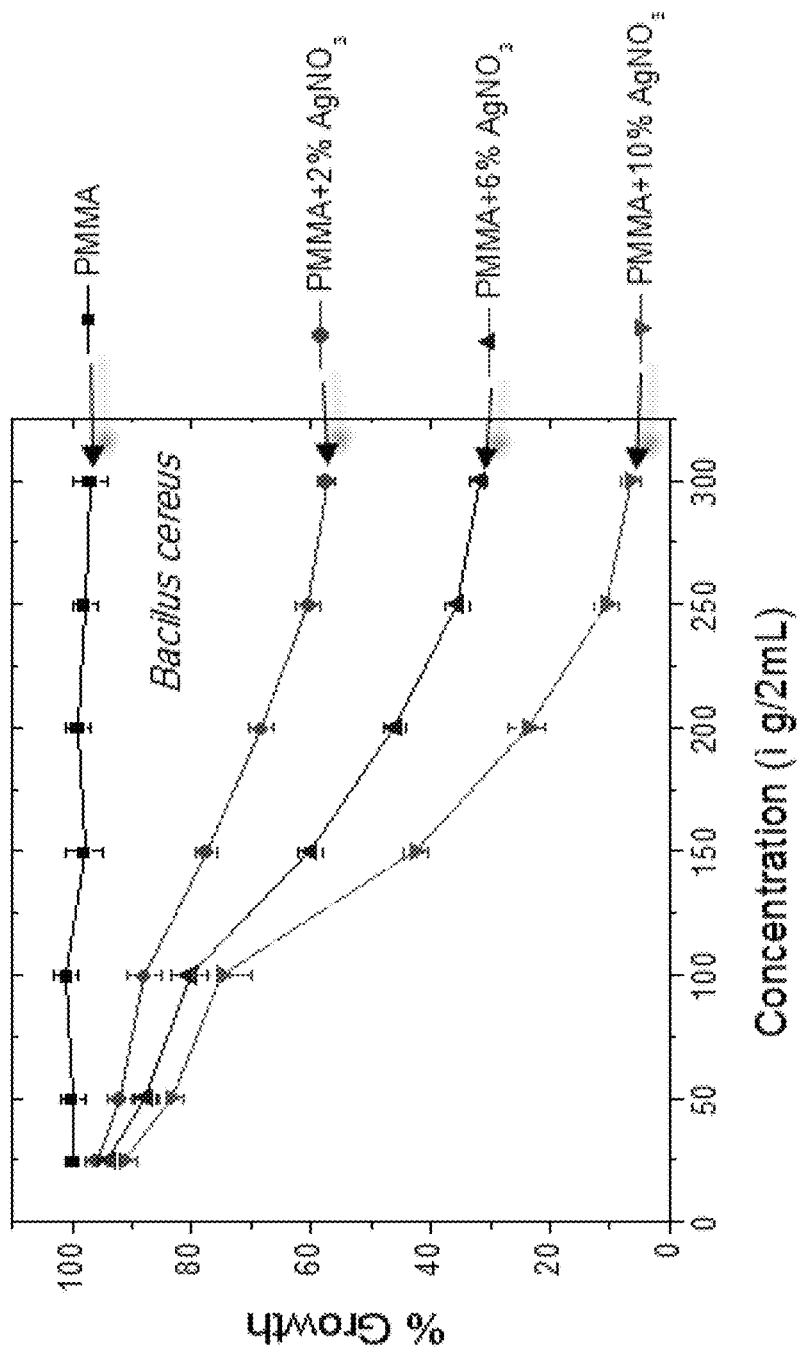
FIG. 11A is a graphical presentation showing the effect of the concentration of the PMMA/Ag nanocomposites prepared with different amounts of $AgNO_3$ on the % growth of the *Bacillus cereus* culture. PMMA, PMMA+2% $AgNO_3$, PMMA+6% $AgNO_3$, and PMMA+10% $AgNO_3$ represent the neat PMMA and the PMMA/silver nanocomposites prepared with 2%, 6%, and 10% by volume relative to the volume of the MMA monomers of 0.1 M $AgNO_3$ dissolved in DMF, respectively.
Figure 11B:
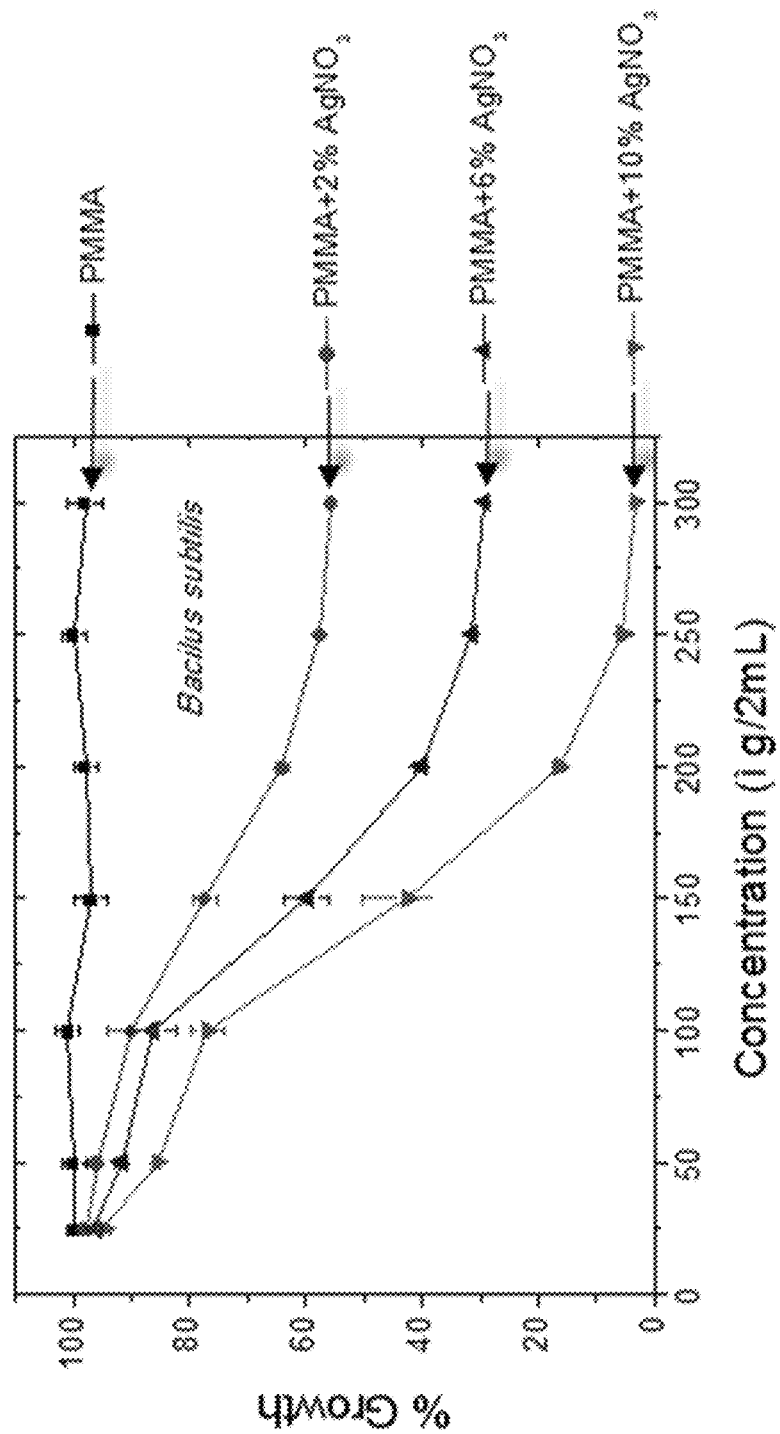
FIG. 11B is a graphical presentation showing the effect of the concentration of the PMMA/Ag nanocomposites prepared with different amounts of $AgNO_3$ on the % growth of the *Bacillus subtilis* culture. PMMA, PMMA+2% $AgNO_3$, PMMA+6% $AgNO_3$, and PMMA+10% $AgNO_3$ represent the neat PMMA and the PMMA/silver nanocomposites prepared with 2%, 6%, and 10% by volume relative to the volume of the MMA monomers of 0.1 M $AgNO_3$ dissolved in DMF, respectively.
Figure 11C:
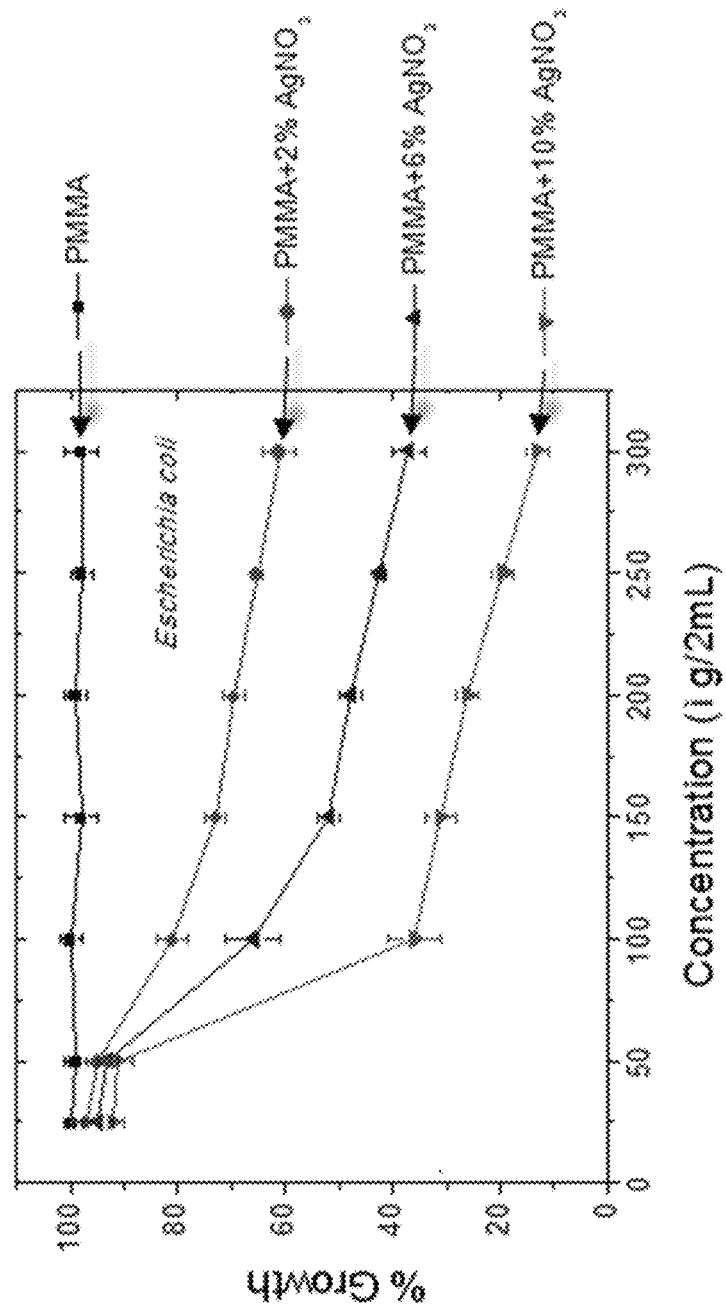
FIG. 11C is a graphical presentation showing the effect of the concentration of the PMMA/Ag nanocomposites prepared with different amounts of $AgNO_3$ on the % growth of the *Escherichia coli* culture. PMMA, PMMA+2% AgNO$_3$, PMMA+6% AgNO$_3$, and PMMA+10% AgNO$_3$ represent the neat PMMA and the PMMA/silver nanocomposites prepared with 2%, 6%, and 10% by volume relative to the volume of the MMA monomers of 0.1 M AgNO$_3$ dissolved in DMF, respectively.
Figure 11D:
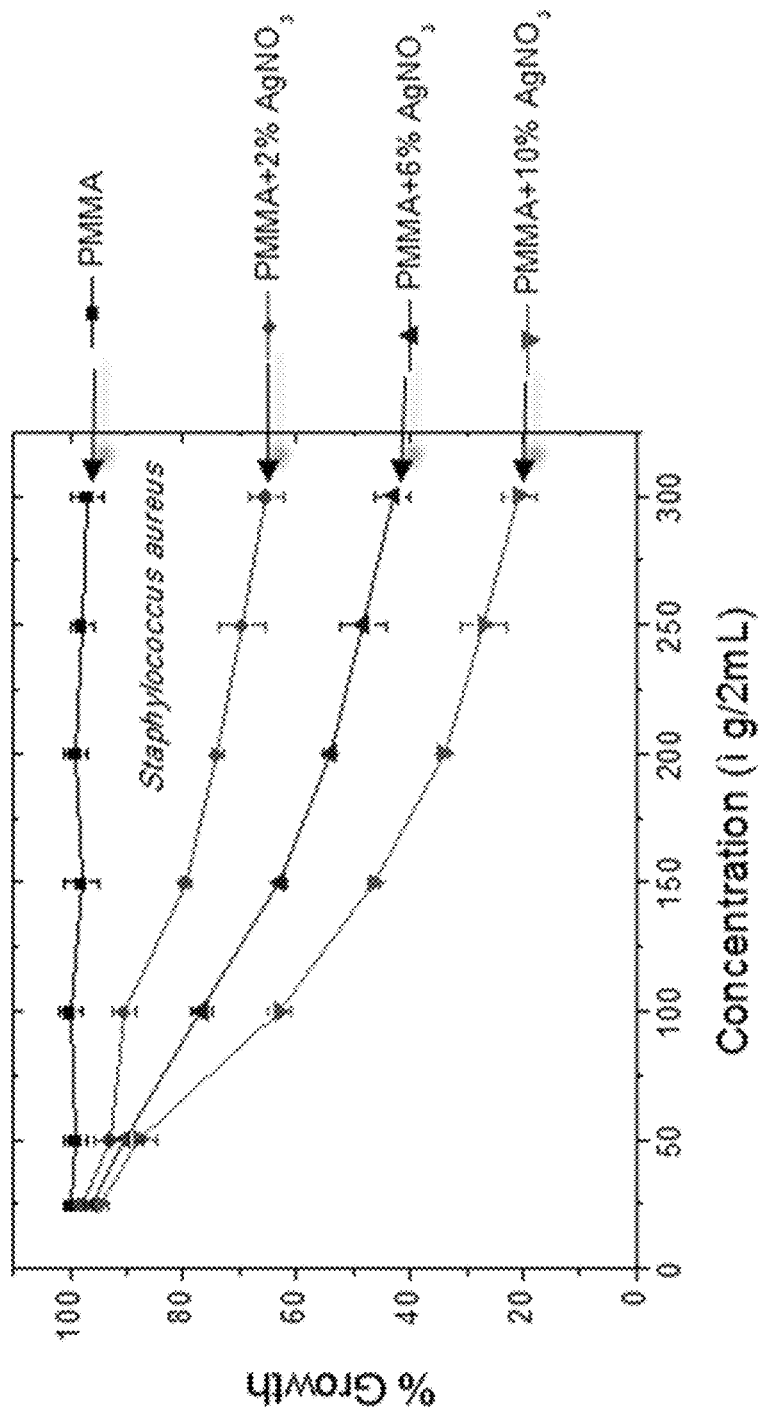
FIG. 11D is a graphical presentation showing the effect of the concentration of the PMMA/Ag nanocomposites prepared with different amounts of AgNO$_3$ on the % growth of the *Staphylococcus aureus* culture. PMMA, PMMA+2% AgNO$_3$, PMMA+6% AgNO$_3$, and PMMA+10% AgNO$_3$ represent the neat PMMA and the PMMA/silver nanocomposites prepared with 2%, 6%, and 10% by volume relative to the volume of the MMA monomers of 0.1 M AgNO$_3$ dissolved in DMF, respectively.
Figure 12:
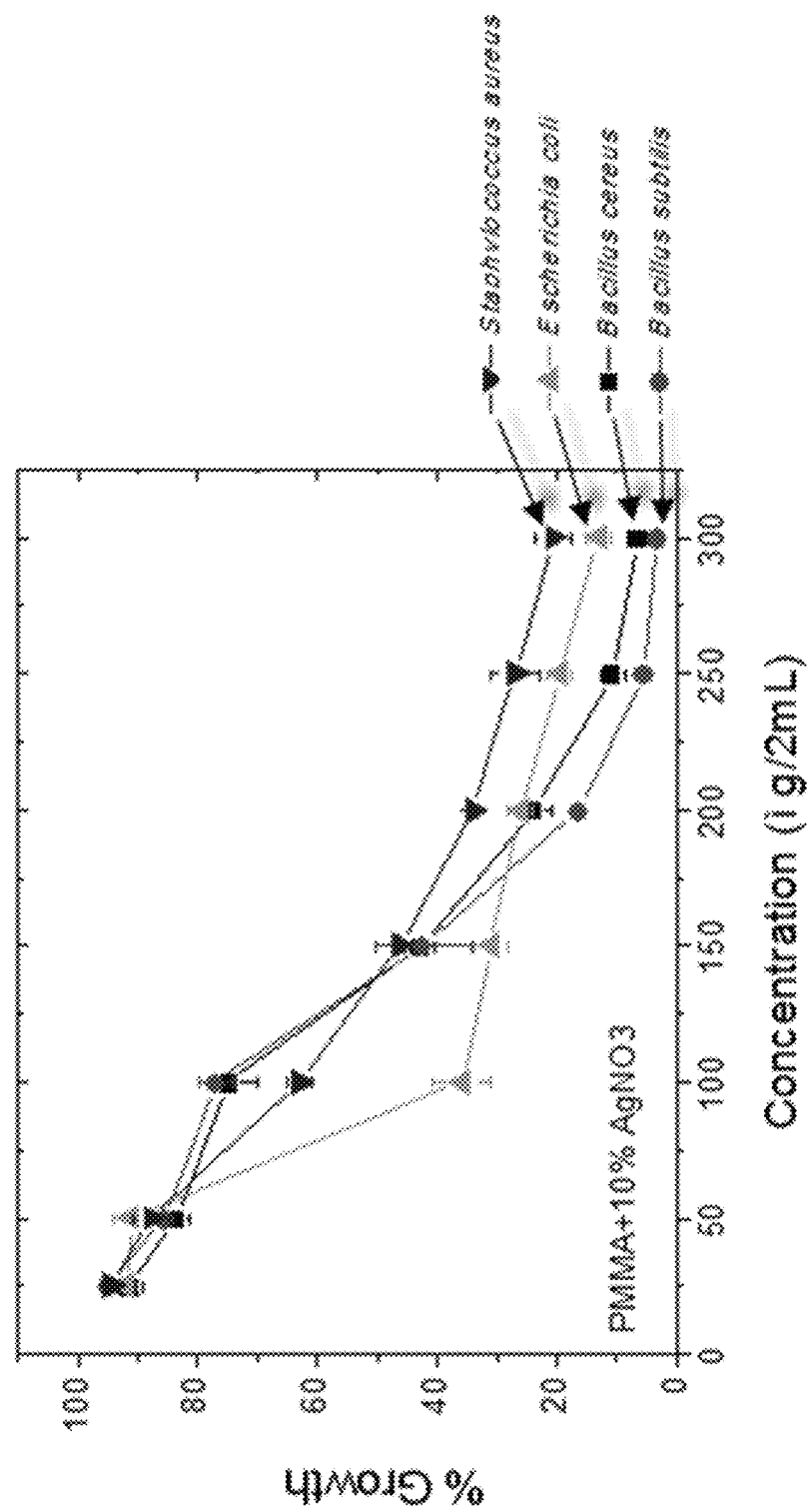
FIG. 12 is a graphical presentation showing the effect of the concentration of PMMA+10% AgNO$_3$—the PMMA/Ag nanocomposite prepared with 10% by volume relative to the volume of the MMA monomers of 0.1 M AgNO$_3$ dissolved in DMF—on the % growth of the *Bacillus cereus, Bacillus subtilis, Escherichia coli*, and *Staphylococcus aureus* culture.

Referring to FIGS. 11A and 11B, the % growth of *Bacillus cereus* and *Bacillus subtilis* reached a value lower than 10% with PMMA+10% $AgNO_3$ at a concentration higher than 250 µg/2 mL, indicating an excellent antibacterial property of the nanocomposite at those concentrations. Referring to FIGS. 11C, 11D, and 12, by comparison, in order to have a comparable % growth reduction of *Escherichia coli* and *Staphylococcus aureus*, PMMA+10% $AgNO_3$ at a concentration higher than 300 µg/2 mL or a PMMA/Ag nanocomposite incorporated with an even higher amount of silver was needed. On the other hand, the neat PMMA did not seem to have any antibacterial activity.

Although the mechanism of the antibacterial action of Ag nanoparticles is still poorly understood, many researchers have reported that Ag nanoparticles can gradually release Ag+ ions which play an important role for antibacterial effects. On the other hand, researchers have reported that spherical Ag nanoparticles had greater antibacterial activity against *E. coli* than Ag+ ions in the form of $AgNO_3$, and proposed that the nanometer size synergistically promoted the antibacterial effect of Ag nanoparticles (S. Pal, Y.-K. Tak and J.-M. Song. Does the Antibacterial Activity of Silver Nanoparticles Depend on the Shape of the Nanoparticle? A Study of the Gram-Negative Bacterium *Escherichia coli. Appl. Environ. Microbiol.* (2007) 73 (6), 1712-1720—incorporated herein by reference in its entirety). In that case, the potential existence of residual Ag+ ions in the PMMA/Ag nanocomposites synthesized in this study may synergistically contribute to the antibacterial activity of Ag nanoparticles despite the small amounts of Ag nanoparticles in the PMMA matrix. The size of the Ag nanoparticles also plays an important role in the antibacterial efficiency of the PMMA/Ag nanocomposites.

In summary, the PMMA/Ag nanocomposites synthesized in this study exhibit antimicrobial activity against four bacterial strains at different concentrations. The incorporation of higher amounts of silver nanoparticles in the polymer matrix results in better antimicrobial activity. Higher amounts of silver nanoparticles incorporated into the polymer matrix may be needed in order to reach the goal of complete inhibition of the bacterial growth.

The invention claimed is:

1. A method of making an antimicrobial poly(methyl methacrylate) (PMMA)/silver nanocomposite comprising PMMA and silver nanoparticles, the method comprising:
    polymerizing methyl methacrylate (MMA) monomer in only one organic solvent and in the presence of only one organic free radical initiator and only one silver salt to form the PMMA by free radical polymerization while reducing in-situ the silver salt to form the silver nanoparticles,
    wherein the MMA is polymerized in a mixture that consists of the MMA, the only one organic solvent, the only one organic free radical initiator, and the only one silver salt,
    wherein the silver nanoparticles have an average particle size of 35-60 nm, and
    wherein the PMMA forms a matrix that encloses the silver nanoparticles, wherein the PMMA/silver nanocomposite has a weight average molecular weight of 280,000-370,000.

2. The method of claim 1, wherein the only one silver salt is one selected from the group consisting of a silver oxide, a silver carbide, a silver nitride, a silver boride, a silver borate, a silver benzoate, a silver sulfide, a silver myristate, a silver stearate, a silver oleate, a silver gluconate, a silver adipate, a silver silicate, a silver sulfate, a silver phosphide, a silver halide, a silver hydride, a silver nitrate, a silver carbonate, a silver sulfadiazine, a silver acetate, a silver lactate, a silver citrate, and an alkali silver thiosulphate.

3. The method of claim 1, wherein the only one organic free radical initiator is one selected from the group consisting of an organic peroxide, a perester, a peroxydicarbonate, and an azo initiator.

4. The method of claim 1, wherein the only one organic free radical initiator is one selected from the group consisting of benzoyl peroxide, dilauroyl peroxide, didecanoyl peroxide, diacetyl peroxide, di(3,5,5-trimethylhexanoyl) peroxide, cumene hydroperoxide, dimethylparatoluidine (DMPT), and allyl thiourea (T).

5. The method of claim 1, wherein the only one organic free radical initiator is one diacyl peroxide at an initial concentration of 0.02-0.04M.

6. The method of claim 1, wherein the silver salt is solely reduced by at least one free radical formed during the free radical polymerization of the MMA monomer.

7. The method of claim 6, wherein the at least one free radical comprises a hydrogen radical.

8. The method of claim 1, wherein the PMMA/silver nanocomposite comprises the silver nanoparticles in an amount of 0.03-0.18% of the total weight of the PMMA/silver nanocomposite.

9. The method of claim 1, wherein the PMMA/silver nanocomposite has a glass transition temperature of 80-95° C.

10. The method of claim 1, wherein the polymerizing is performed at a temperature of 70-90° C.

11. The method of claim 1, wherein the only one organic solvent is dimethylformamide (DMF), dimethylaminoethyl methacrylate (DMAEMA), benzene, naphthalene, a substituted benzene, or a substituted naphthalene.

12. The method of claim 1, wherein the only one organic solvent is dimethylformamide.

13. The method of claim 1, wherein the only one organic solvent is present at a volume percentage of 2-10 vol % relative to a volume of the MMA monomer.

14. The method of claim 1, further comprising stopping the polymerizing by adding hydroquinone to the mixture.

15. The method of claim 1, further comprising isolating the PMMA/silver nanocomposite by dissolving the PMMA/silver nanocomposite in $CH_2Cl_2$ and reprecipitating in methanol.

16. The method of claim 1, wherein the polymerizing forms a solid mass of the PMMA/silver nanocomposite.

* * * * *